(12) United States Patent  
Scheib et al.

(10) Patent No.: US 10,743,866 B2  
(45) Date of Patent: *Aug. 18, 2020

(54) TRANS-ORAL CIRCULAR ANVIL INTRODUCTION SYSTEM WITH DILATION FEATURE

(71) Applicant: Ethicon LLC, Guaynabo, PR (US)

(72) Inventors: Charles J. Scheib, Loveland, OH (US); John P. Measamer, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 643 days.

This patent is subject to a terminal disclaimer.

(21) Appl. No.: 15/214,839

(22) Filed: Jul. 20, 2016

(65) Prior Publication Data

US 2016/0324525 A1    Nov. 10, 2016

Related U.S. Application Data

(63) Continuation of application No. 13/693,430, filed on Dec. 4, 2012, now Pat. No. 9,572,573.

(51) Int. Cl.
*A61B 17/115* (2006.01)
*A61B 17/11* (2006.01)
(Continued)

(52) U.S. Cl.
CPC ........ *A61B 17/068* (2013.01); *A61B 17/1114* (2013.01); *A61B 17/1155* (2013.01);
(Continued)

(58) Field of Classification Search
CPC ............. A61B 17/1114; A61B 17/1155; A61B 17/068; A61B 2017/00278;
(Continued)

(56) References Cited

U.S. PATENT DOCUMENTS 4,805,823 A    2/1989 Rothfuss  
4,817,847 A    4/1989 Redtenbacher et al.  
(Continued)

FOREIGN PATENT DOCUMENTS

CN    102711653 A    10/2012  
DE    87 14 082       2/1988  
(Continued)

OTHER PUBLICATIONS

International Preliminary Report on Patentability dated Jun. 9, 2015 re PCT/US2013/073097.

(Continued)

*Primary Examiner* — Thanh K Truong  
*Assistant Examiner* — Thomas M Wittenschlaeger  
(74) *Attorney, Agent, or Firm* — Frost Brown Todd LLC

(57) ABSTRACT

An anvil introduction system is operable to provide smooth insertion of an anvil of a surgical stapling device through a bodily lumen such as the esophagus. The anvil introduction system is coupled to the anvil and includes a dilation feature. The dilation feature has a collapsed position and an expanded position. The dilation feature may cover staple pockets and an outer edge of the anvil with the dilation feature is in the expanded position. The anvil may be inserted through the bodily lumen with the dilation feature in the expanded position. The dilation feature may then be collapsed in order to complete an end-to-end anastomosis of the bodily lumen.

9 Claims, 21 Drawing Sheets

(51) Int. Cl.
*A61B 17/068* (2006.01)
*A61B 17/00* (2006.01)
*A61B 17/072* (2006.01)
*A61B 34/30* (2016.01)
*A61B 90/00* (2016.01)

(52) U.S. Cl.
CPC ..... *A61B 34/30* (2016.02); *A61B 2017/00278* (2013.01); *A61B 2017/00473* (2013.01); *A61B 2017/00557* (2013.01); *A61B 2017/00818* (2013.01); *A61B 2017/0725* (2013.01); *A61B 2017/1132* (2013.01); *A61B 2017/1142* (2013.01); *A61B 2017/1157* (2013.01); *A61B 2090/08021* (2016.02); *A61B 2217/007* (2013.01)

(58) Field of Classification Search
CPC .... A61B 2017/0725; A61B 2017/1157; A61B 2017/00818; A61B 2017/1142; A61B 2017/1132; A61B 2017/00557; A61B 2017/00473; A61B 2090/08021; A61B 2217/007; A61B 34/30
See application file for complete search history.

(56) References Cited

U.S. PATENT DOCUMENTS

| | | | |
|---|---|---|---|
| 4,873,977 A * | 10/1989 | Avant | A61B 17/115 227/180.1 |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,944 A * | 2/1994 | Green | A61B 17/115 227/121 |
| 5,285,945 A | 2/1994 | Brinkerhoff et al. | |
| 5,292,053 A | 3/1994 | Bilotti et al. | |
| 5,314,435 A * | 5/1994 | Green | A61B 17/115 227/175.1 |
| 5,333,773 A | 8/1994 | Main et al. | |
| 5,350,104 A | 9/1994 | Main et al. | |
| 5,360,154 A * | 11/1994 | Green | A61B 17/115 227/179.1 |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 5,836,503 A * | 11/1998 | Ehrenfels | A61B 17/115 227/175.1 |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,179,267 B2 * | 2/2007 | Nolan | A61B 17/1114 227/175.1 |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,529,591 B2 | 9/2013 | Nakamura et al. | |
| 9,522,002 B2 * | 12/2016 | Chowaniec | A61B 17/068 |
| 9,572,573 B2 * | 2/2017 | Scheib | A61B 17/1155 |
| 9,717,515 B1 * | 8/2017 | McCarty | A61B 17/221 |
| 2003/0014064 A1 | 1/2003 | Blatter | |
| 2005/0070921 A1 * | 3/2005 | Ortiz | A61B 17/1114 606/139 |
| 2006/0201989 A1 | 9/2006 | Ojeda | |
| 2009/0082789 A1 * | 3/2009 | Milliman | A61B 17/115 606/148 |
| 2010/0130993 A1 * | 5/2010 | Paz | A61B 17/11 606/153 |
| 2010/0163598 A1 * | 7/2010 | Belzer | A61B 17/115 227/181.1 |
| 2014/0151429 A1 | 6/2014 | Scheib et al. | |
| 2014/0166720 A1 * | 6/2014 | Chowaniec | A61B 17/068 227/176.1 |
| 2016/0317146 A1 * | 11/2016 | Kelley | A61B 17/1155 |

FOREIGN PATENT DOCUMENTS

| | | |
|---|---|---|
| GB | 2 038 692 | 7/1980 |
| JP | H11-004832 A | 1/1999 |
| JP | 2004-515258 A | 5/2004 |
| JP | 2007-533397 A | 11/2007 |
| JP | 2009-082727 A | 4/2009 |
| JP | 2012-183321 A | 9/2012 |
| WO | WO 01/66020 | 9/2001 |
| WO | WO 2008/089404 | 7/2008 |

OTHER PUBLICATIONS

International Search Report dated May 6, 2014 for Application No. PCT/US2013/073097.
Japanese Office Action, Notification of Reasons for Refusal, dated Mar. 13, 2018 for Application No. JP 2015-545817, 4 pgs.
Japanese Office Action, Notification of Reasons for Refusal, dated Jul. 18, 2017 for Application No. JP 2015-545817, 5 pgs.
Chinese Office Action, The First Office Action, and Search Report dated Dec. 23, 2016 for Application No. CN 201380063907.6, 10 pgs.
Japanese Search Report by Registered Search Organization dated Jul. 21, 2017 for Application No. JP 2015-545817, 11 pgs.
Japanese Office Action, Decision to Grant a Patent, dated Jun. 19, 2018 for Application No. JP 2015-545817, 2 pgs.

* cited by examiner

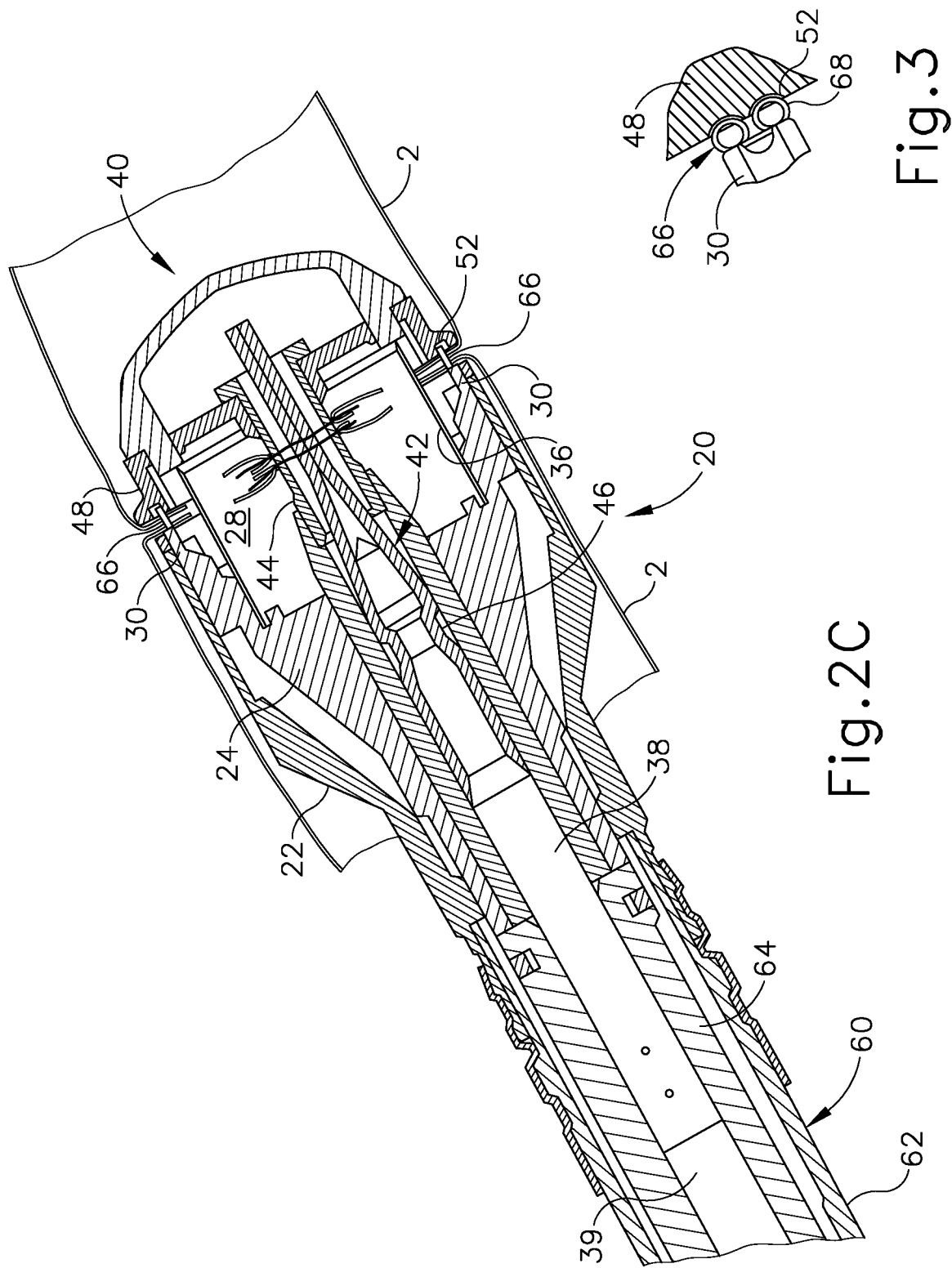

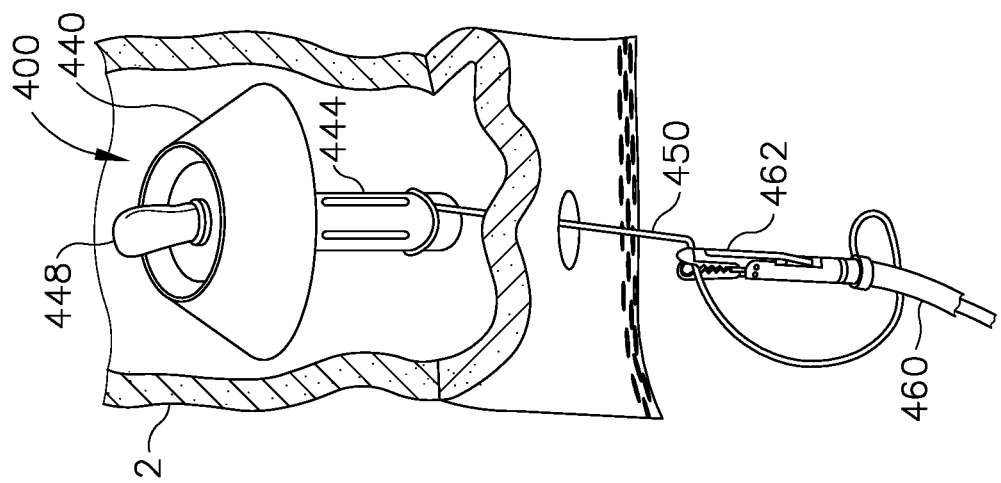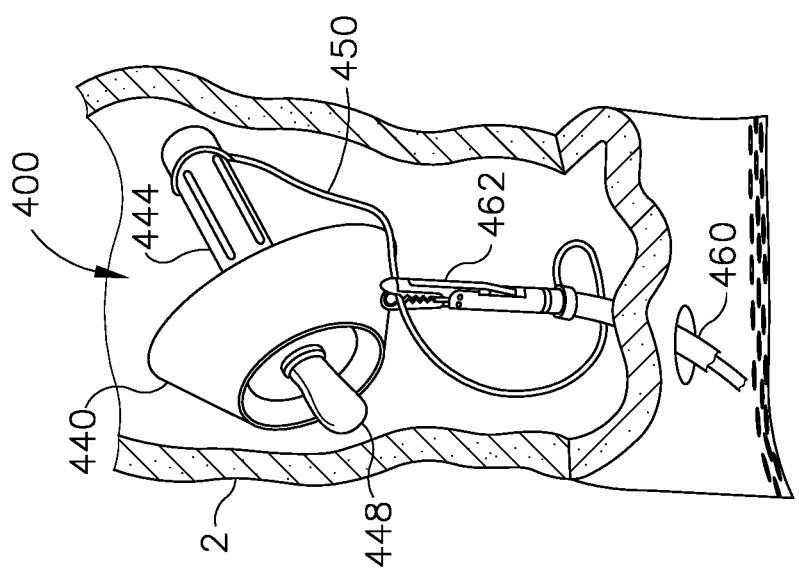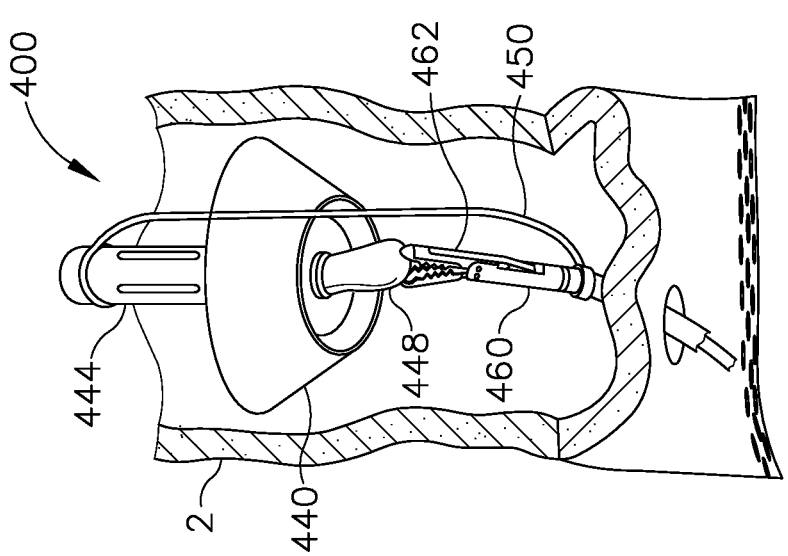

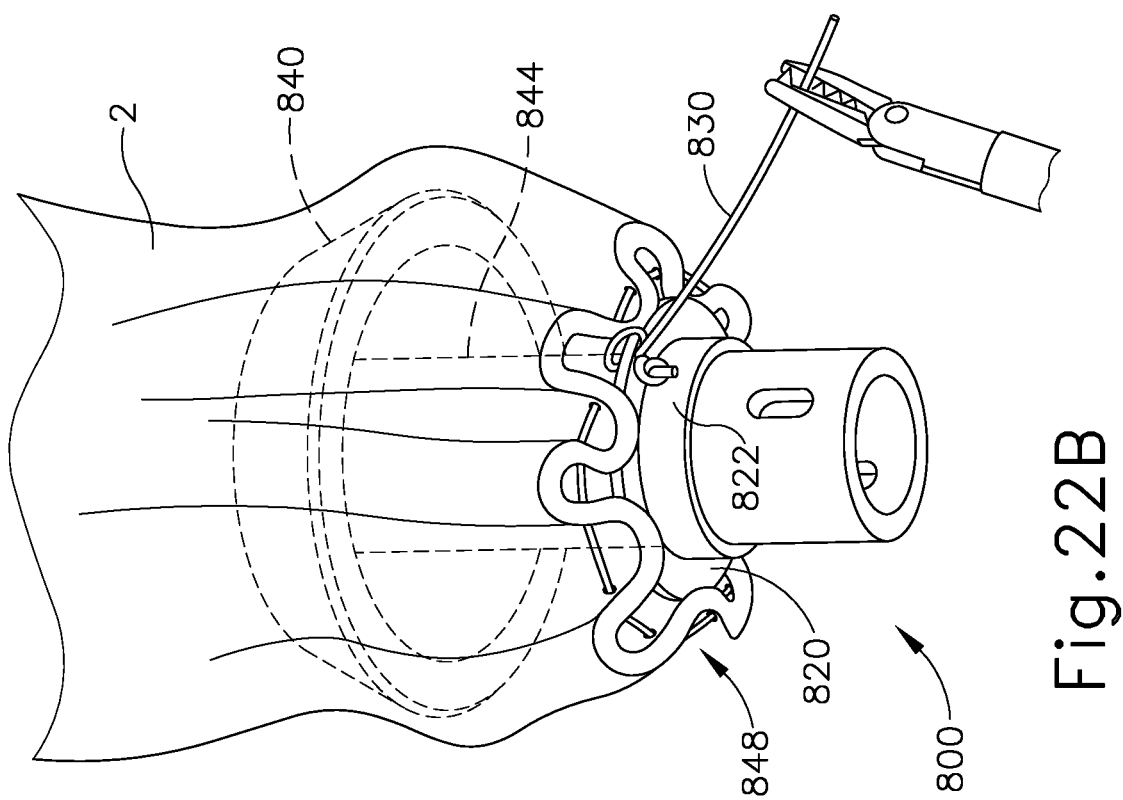
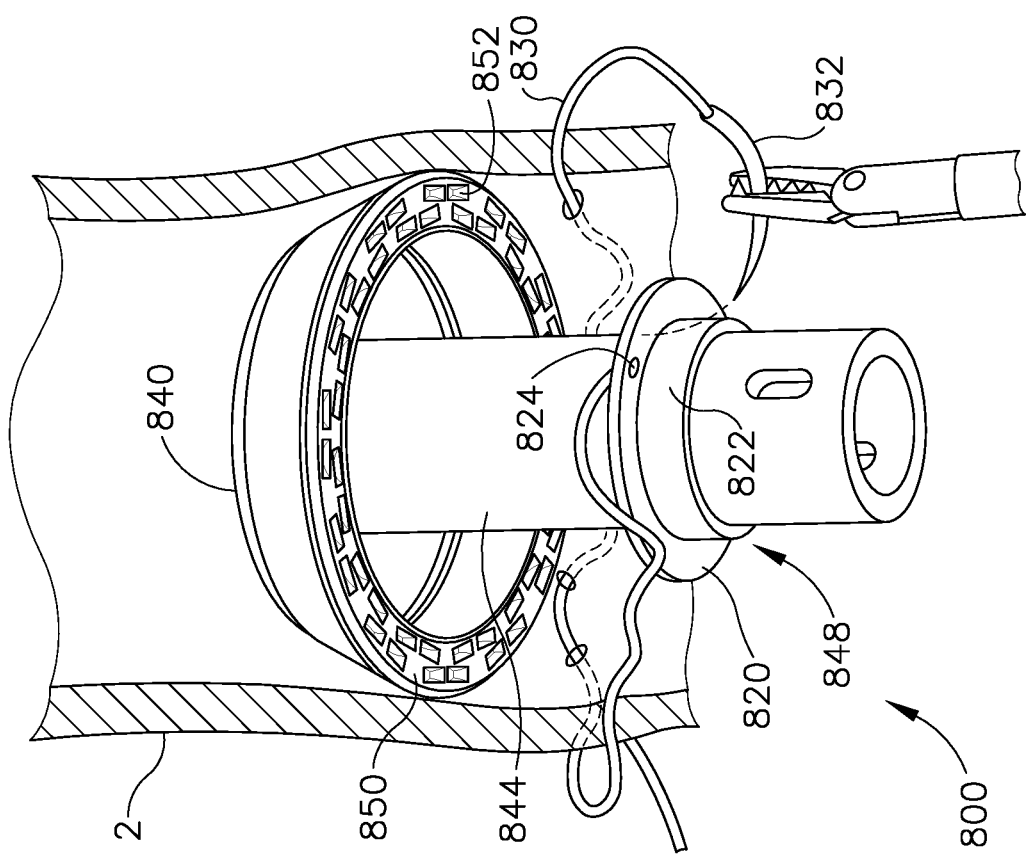

TRANS-ORAL CIRCULAR ANVIL INTRODUCTION SYSTEM WITH DILATION FEATURE

This application is a continuation of U.S. patent application Ser. No. 13/693,430, entitled "Trans-Oral Circular Anvil Introduction System with Dilation Feature," filed on Dec. 4, 2012, published as U.S. Pub. No. 2014/0151429 on Jun. 5, 2014, issued as U.S. Pat. No. 9,572,573 on Feb. 21, 2017.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 19A depicts an enlarged partial perspective view of the anvil of FIG. 18, showing the anvil in an introduction position within a lumen;

FIG. 19B depicts an enlarged partial perspective view of the anvil of FIG. 18, showing rotation of the anvil within the lumen;

FIG. 19C depicts an enlarged partial perspective view of the anvil of FIG. 18, showing the anvil approaching a stapling position within the lumen;

FIG. 22A depicts an enlarged partial perspective view of an exemplary anvil securing feature within a lumen, showing the lumen being sutured in a purse-string configuration; and FIG. 22B depicts an enlarged partial perspective view of the anvil securing feature of FIG. 22A showing the lumen in a cinched position and secured to the anvil by the suture.

Figure 6:
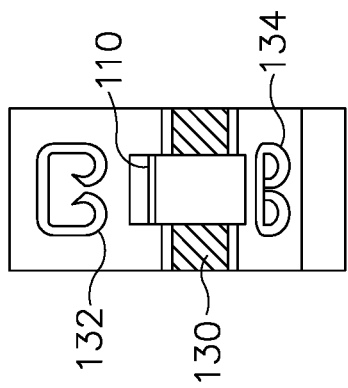
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
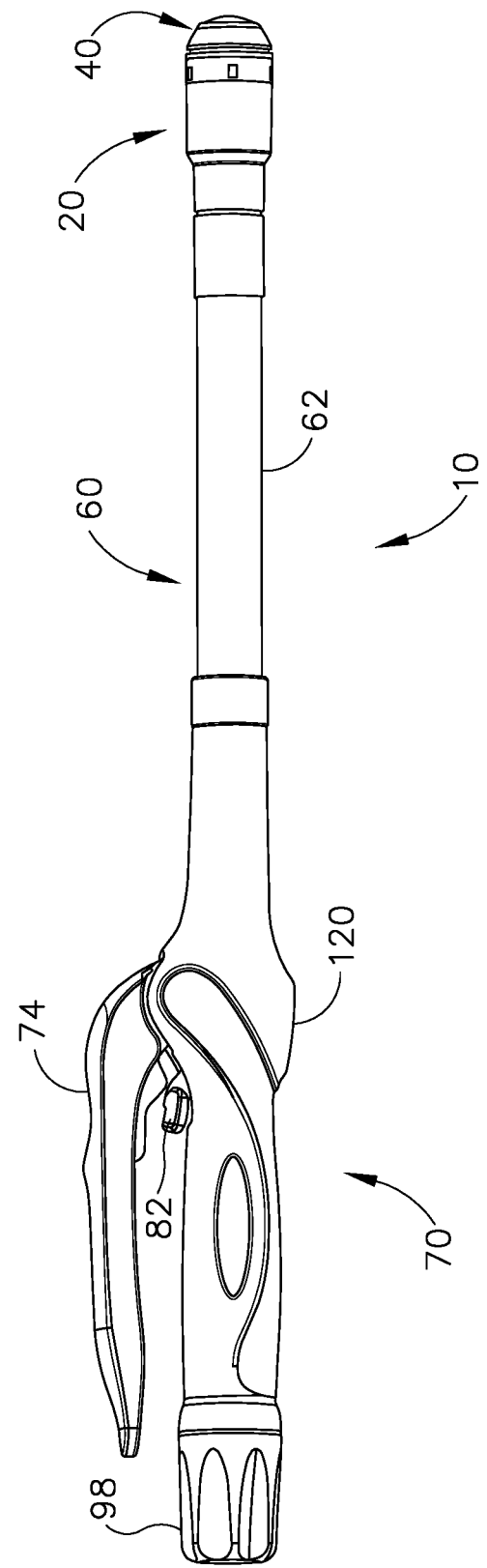
FIG. 1 depicts a side elevation view of an exemplary circular stapling surgical instrument.
Figure 2A:
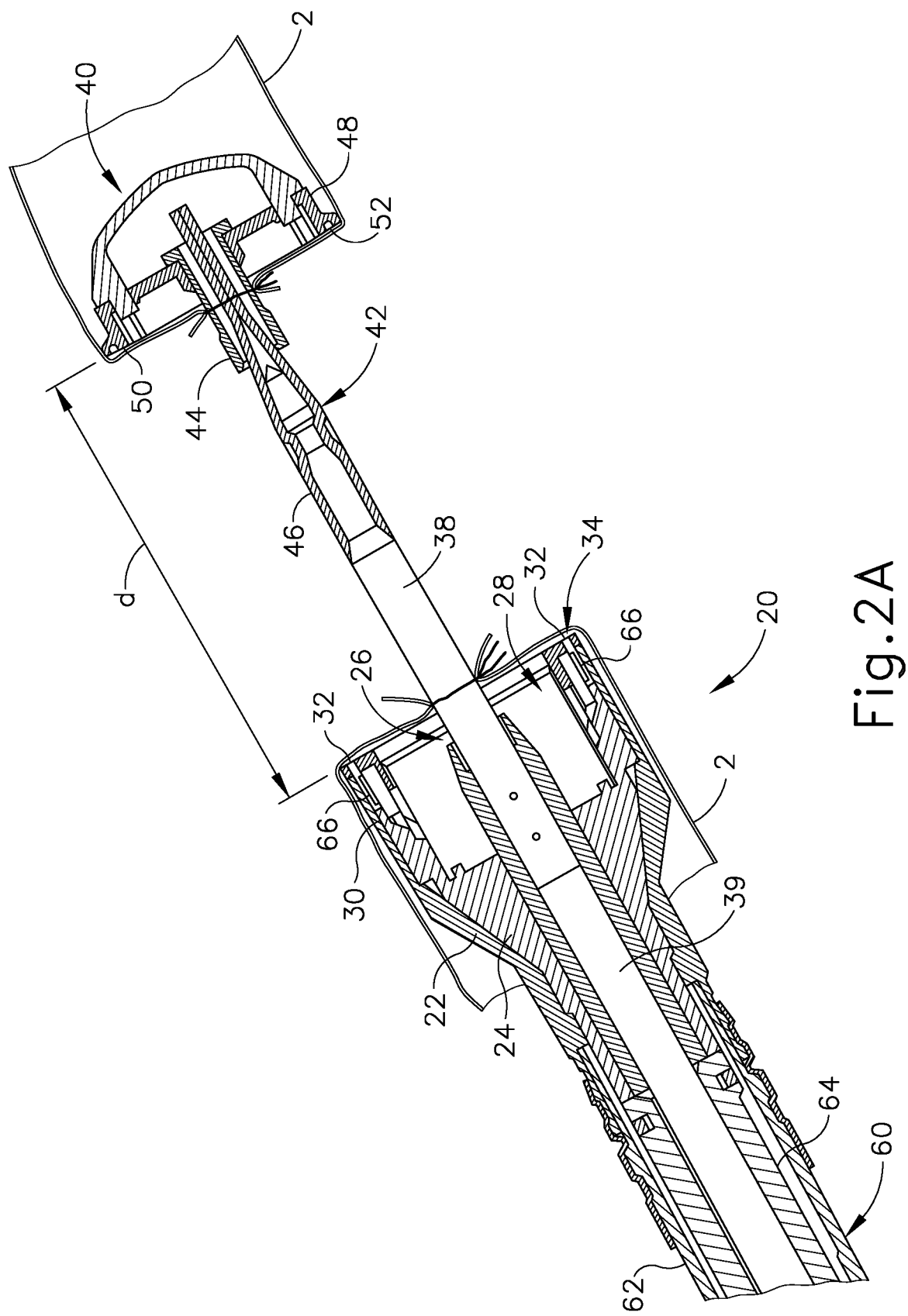
FIG. 2A depicts an enlarged longitudinal cross-section view of an exemplary stapling head assembly of the instrument of FIG. 1 showing an exemplary anvil in an open position.
Figure 2B:
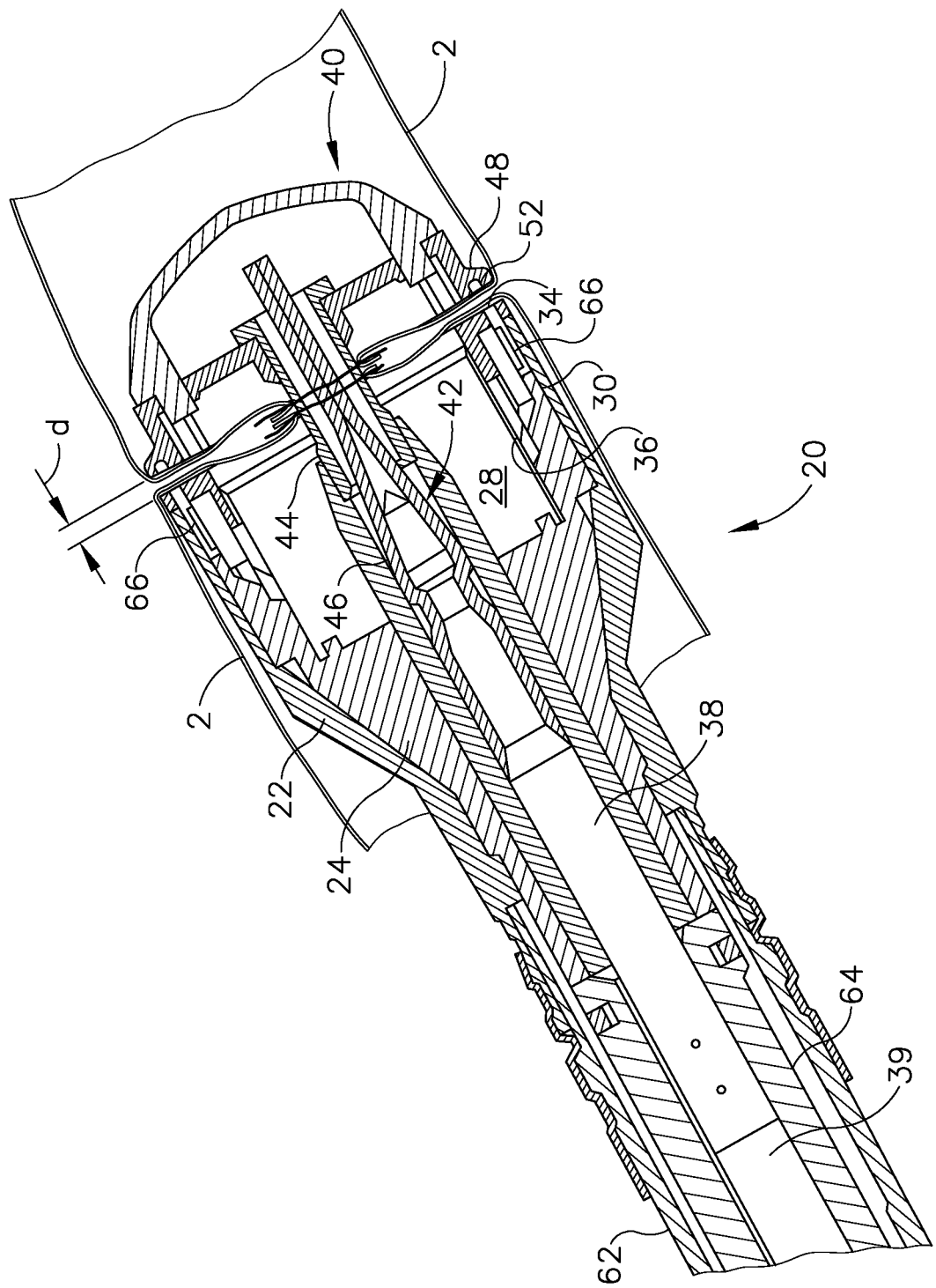
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38).

Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below. In some other versions, stapling head assembly (20) is actuated via motor or is otherwise powered.

Figure 5:
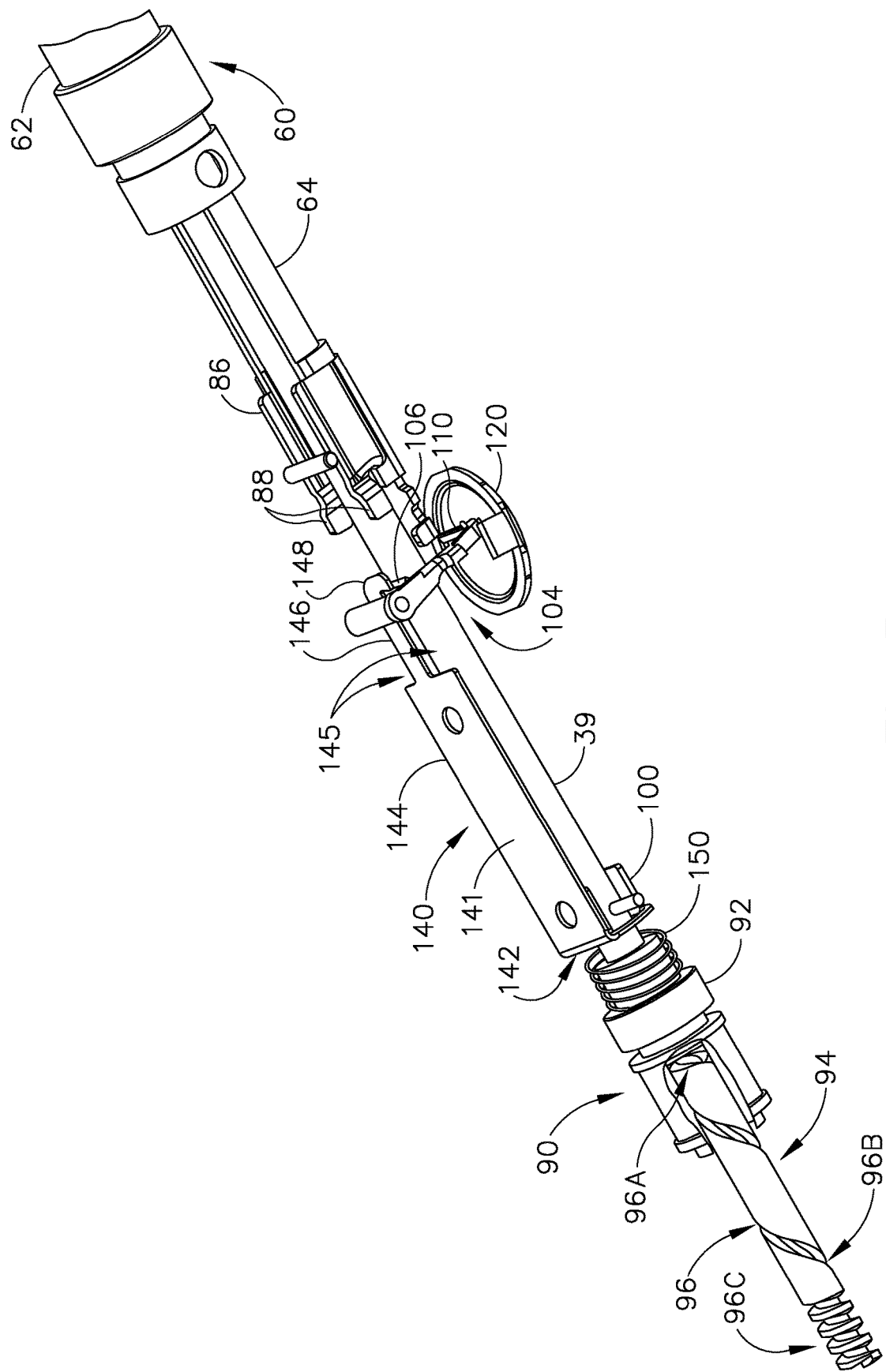
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
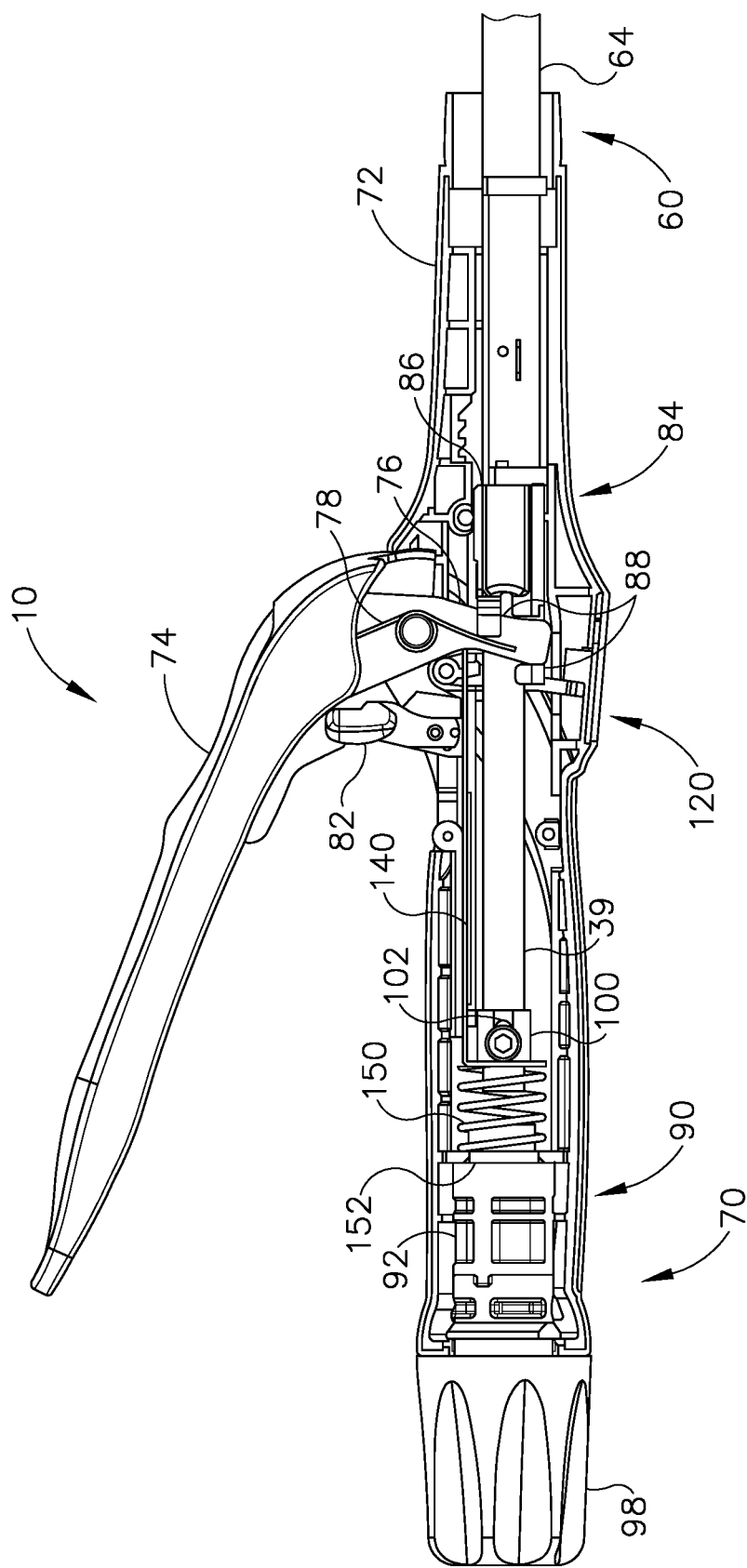
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
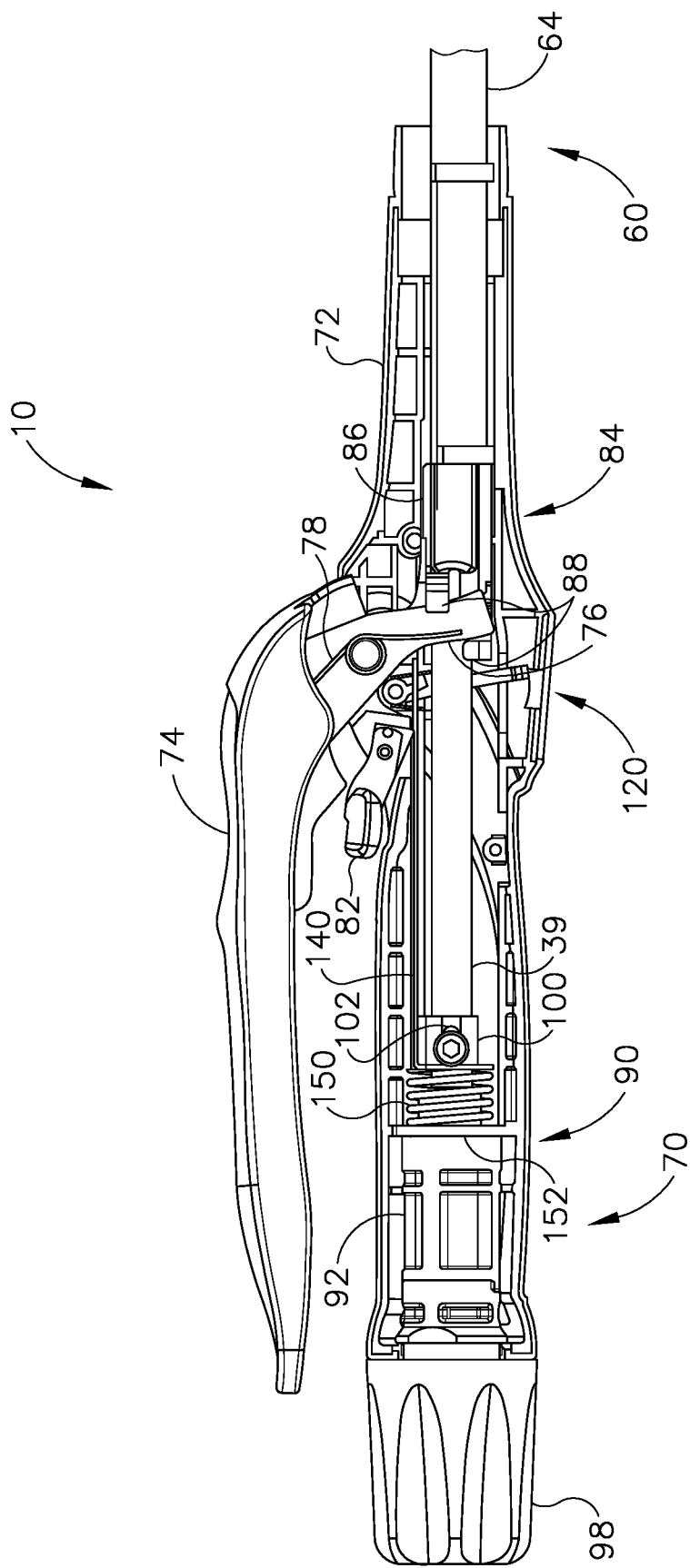
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64)

while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773;. 5,350,104; 5,533,661, the disclosures of which are incorporated by reference herein; and/or in accordance with other configurations as will be apparent to one of ordinary skill in the art in view of the teachings herein.

II. Exemplary Trans-Oral Circular Anvil Introduction System

Figure 7:
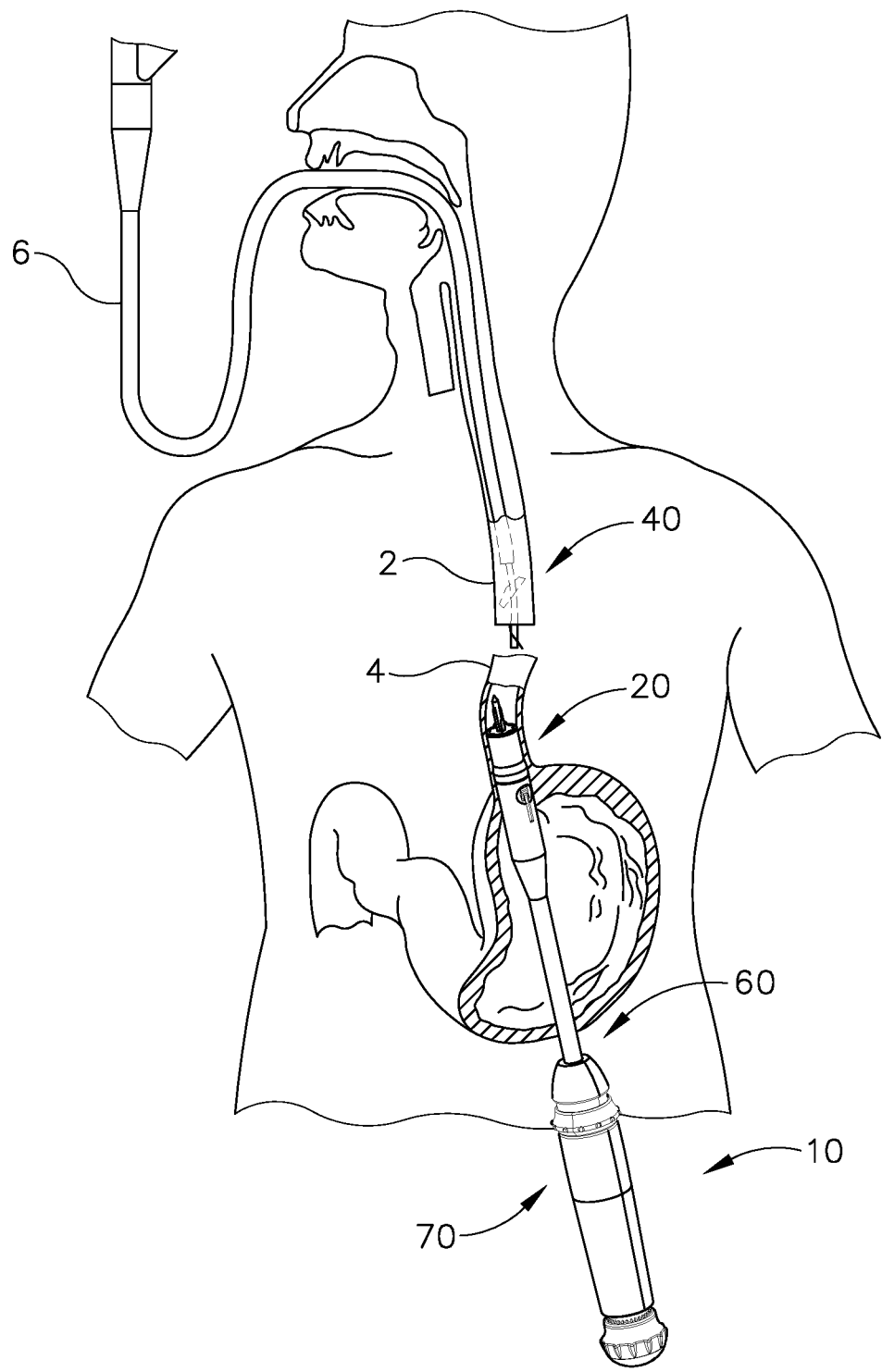
FIG. 7 depicts a schematic view of an exemplary circular stapler system being used in an esophagectomy procedure.

As described above, anvil (40) may be provided as a separate component such that anvil (40) may be inserted and secured to a portion of tissue (2) prior to being coupled to stapling head assembly (20). For instance, it may be desirable to introduce anvil (40) trans-orally for procedures within a patient's gastro-intestinal tract (e.g., an esophagectomy). FIG. 7 depicts an initial stage of an anastomosis procedure to couple severed esophagus sections (2, 4) following an esophagectomy. Anvil (40) is inserted trans-orally through the esophagus using an endoscope (6) and is positioned within a first severed section (2) of the esophagus. Instrument (10) is inserted through the stomach and positioned within a second severed section (4) of the esophagus. Anvil (40) is then coupled to trocar (38) of instrument (10) to staple and seal severed sections (2, 4) of the esophagus in an anastomosis. Anvil (40) may also be inserted within other bodily lumens or regions of the gastro-intestinal tract to perform an anastomosis as will be apparent to one with ordinary skill in the art in view of the teachings herein. Because improper introduction of anvil (40) may irritate the esophagus, it may be desirable to provide a trans-oral circular anvil introduction system to smoothly insert anvil (40) through the bodily lumen. An anvil introduction system may comprise dilation features to cover at least the proximal side of anvil (40) during insertion, if not the entire anvil (40) during insertion; or the system may comprise anvil grasping features to insert anvil (40) upside-down such that the proximal side of anvil (40) faces away from tissue. Various examples of such features will be described in greater detail below, while other examples will be apparent to one with ordinary skill in the art in view of the teachings herein.

A. Exemplary Dilation Features

An anvil introduction system may comprise anvil dilation features that either inflate or expand to cover the proximal side of anvil (40) during insertion. Such dilation features may prevent an outer perimeter edge at the proximal side of anvil (40) from dragging along the inner wall of the esophagus as anvil (40) is transported through the esophagus to reach the desired anastomosis site. Various examples of such features will be described in greater detail below, while other examples will be apparent to one with ordinary skill in the art in view of the teachings herein.

1. Exemplary Inflatable Feature

Figure 8:
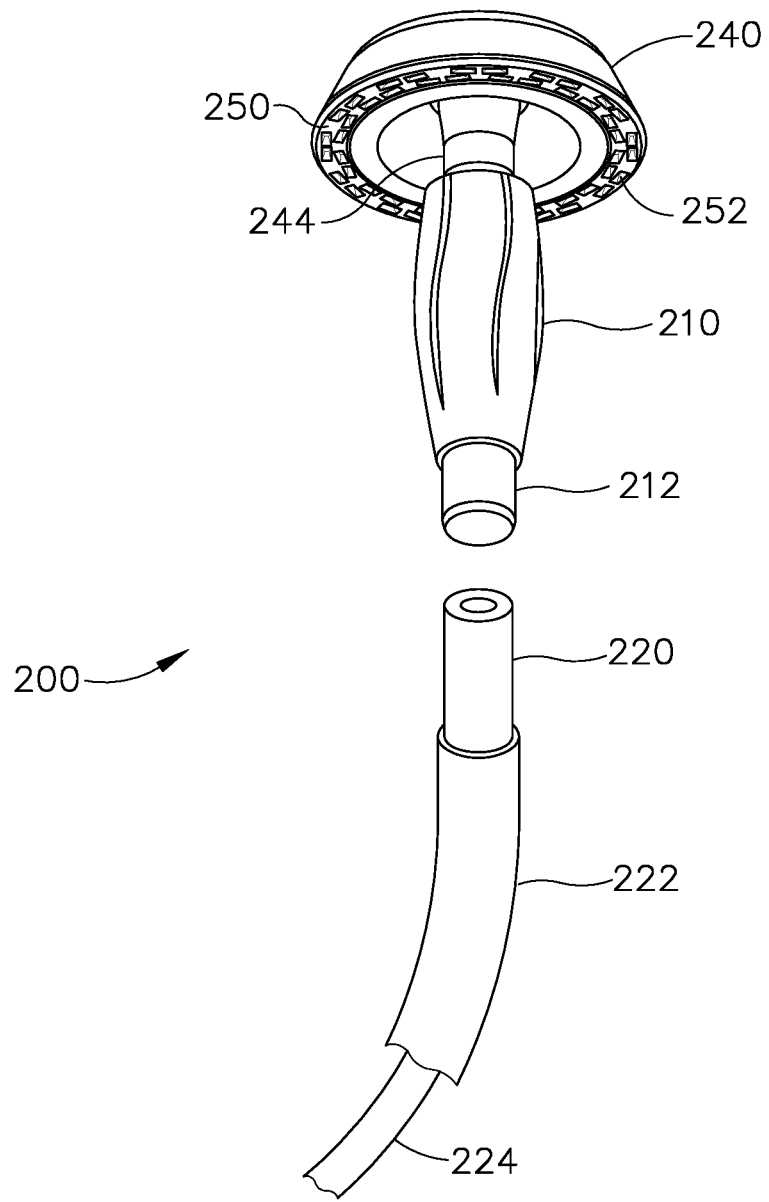
FIG. 8 depicts an enlarged partial perspective view of an exemplary trans-oral circular anvil introduction system showing a dilation feature in a deflated state.
Figure 9B:
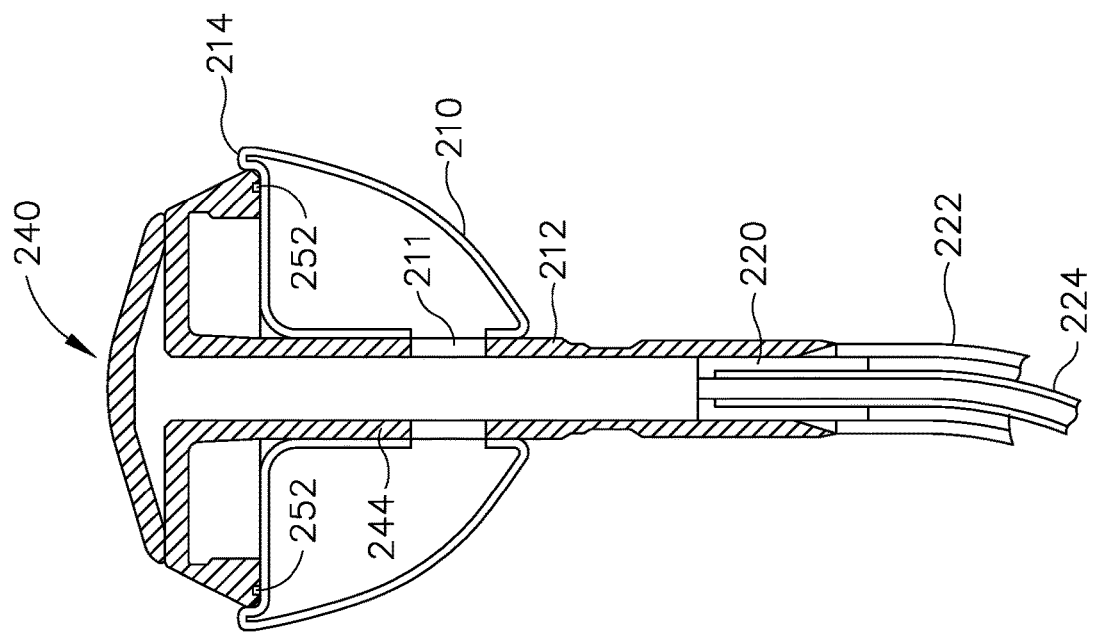
FIG. 9B depicts a cross sectional view of the anvil introduction system of FIG. 7 showing the dilation feature in an inflated state.
Figure 9A:
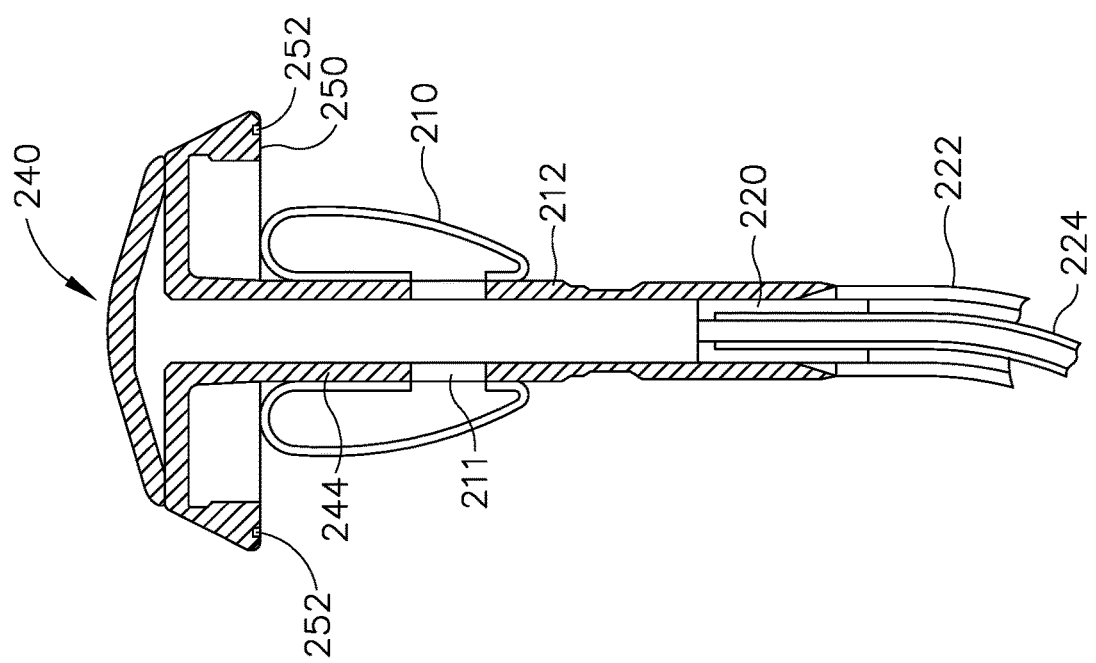
FIG. 9A depicts a cross sectional view of the anvil introduction system of FIG. 7 showing the dilation feature in the deflated state.
Figure 10:
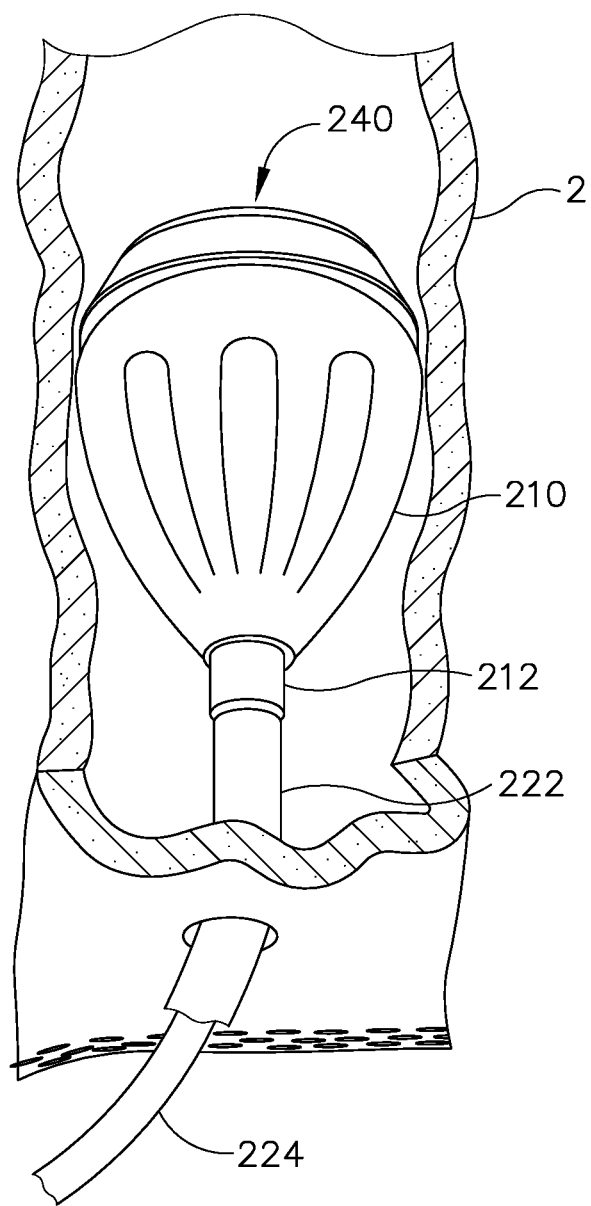
FIG. 10 depicts an enlarged partial perspective view of the anvil introduction system of FIG. 7 showing the dilation feature in the inflated state passing through a lumen.
Figure 12:
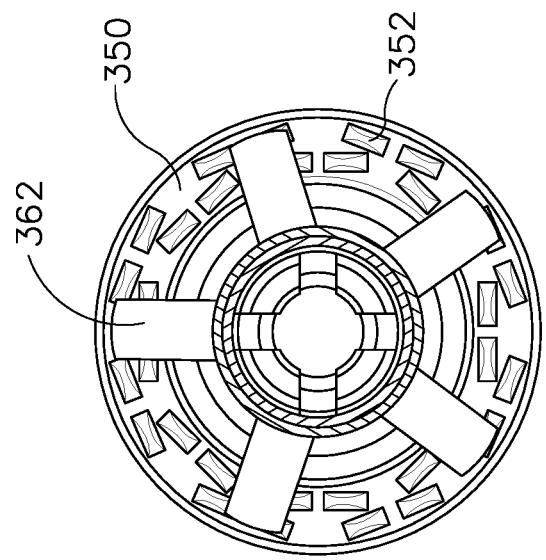
FIG. 12 depicts a cross sectional view of the anvil introduction system of FIG. 11 taken along the line 12-12 of FIG. 11.

An exemplary trans-oral circular anvil introduction system (200) is shown in FIGS. 8-10. Anvil introduction system (200) of the present example comprises a dilation feature, such as inflatable bladder (210), which is expandable around anvil (240) to cover any sharp edges of anvil (240) during the introduction of anvil (240) through a naturally occurring bodily lumen (e.g. the esophagus). For example, anvil introduction system (200) comprises an anvil (240), an inflatable bladder (210), and a flexible tube (222), as shown in FIG. 8. Anvil (240) is similar to anvil (40) described above. Anvil (240) comprises staple pockets (252) aligned on proximal surface (250) of anvil (240). Anvil (240) also comprises a proximally extending shaft (244). Shaft (244) is coupled to inflatable bladder (210). Inflatable bladder (210) comprises a flexible membrane that wraps around shaft (244) and inflates to cover staple pockets (252) and the edge of proximal surface (250) of anvil (240), as shown in FIG. 9B. In the inflated state, bladder (210) defines a tapered shape from anvil (240). Apertures (211) are provided in shaft (244) to allow air, saline, or other fluid to pass through shaft (244) to inflate bladder (210). Tubular member (212) extends from bladder (210) to selectively couple bladder (210) to flexible tube (222). Shaft (244) is similar to proximal shaft (42) of anvil (40) such that shaft (244) is configured to couple with trocar (38) once anvil (240) is positioned for stapling.

Flexible tube (222) comprises a snap feature (220) and an inflation tube (224). Snap feature (220) extends from the distal end of flexible tube (222). Snap feature (220) comprises a smaller diameter than tubular member (212) such that snap feature (220) slides or snaps into tubular member (212) to couple flexible tube (222) to tubular member (212), as shown in FIG. 9A. Snap feature (220) may also have a larger diameter than tubular member (212) such that snap feature (220) slides around tubular member (212). Snap feature (220) may also be sutured to tubular member (212). Other suitable methods to couple flexible tube (222) to tubular member (212) will be apparent to one with ordinary skill in the art based on the teachings herein. Inflation tube (224) is positioned within flexible tube (222). Inflation tube (224) may be used to inject fluid into bladder (210) to inflate bladder (210). However, inflation tube (224) is merely optional and flexible tube (222) may be used to inject fluid into bladder (210). Flexible tube (222) may comprise a conventional NG (naso-gastric) tube or any other suitable structure.

As shown in FIG. 9A, snap feature (220) is inserted into tubular member (212) to couple flexible tube (222) to tubular member (212). Once coupled, inflation tube (224) introduces fluid into bladder (210) to inflate bladder (210), as shown in FIG. 9B. With bladder (210) inflated, bladder (210) covers staple pockets (252). Bladder (210) also extends past anvil (240) to form an annular protrusion (214) to cover the edge of proximal surface (250) of anvil (240). In the inflated state, flexible tube (222) is used to pull anvil (240) smoothly through a naturally occurring bodily lumen (e.g., the esophagus), as shown in FIG. 10. Once anvil (240) is positioned by anvil introduction system (200), bladder (210) is deflated by passing the fluid back through inflation tube (224). Flexible tube (222) is then be removed from anvil (240), and anvil (240) is coupled to trocar (38) of circular surgical stapling instrument (10) for operation.

2. Exemplary Expandable Mesh Feature

Figure 14:
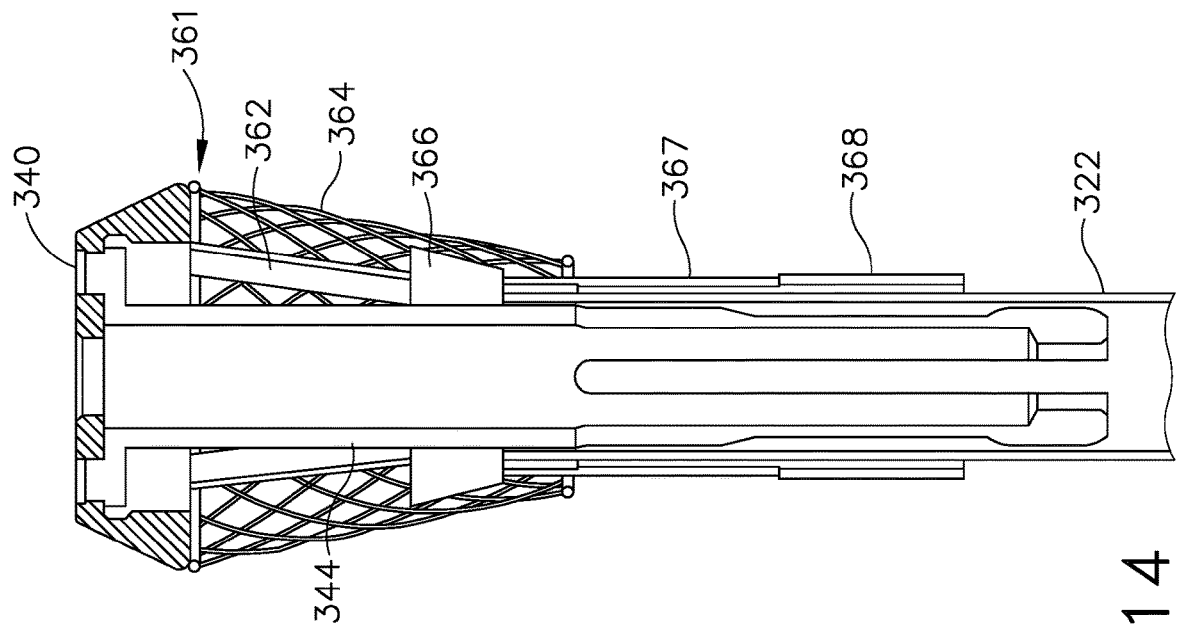
FIG. 14 depicts a cross sectional view of the anvil introduction system of FIG. 13.
Figure 15:
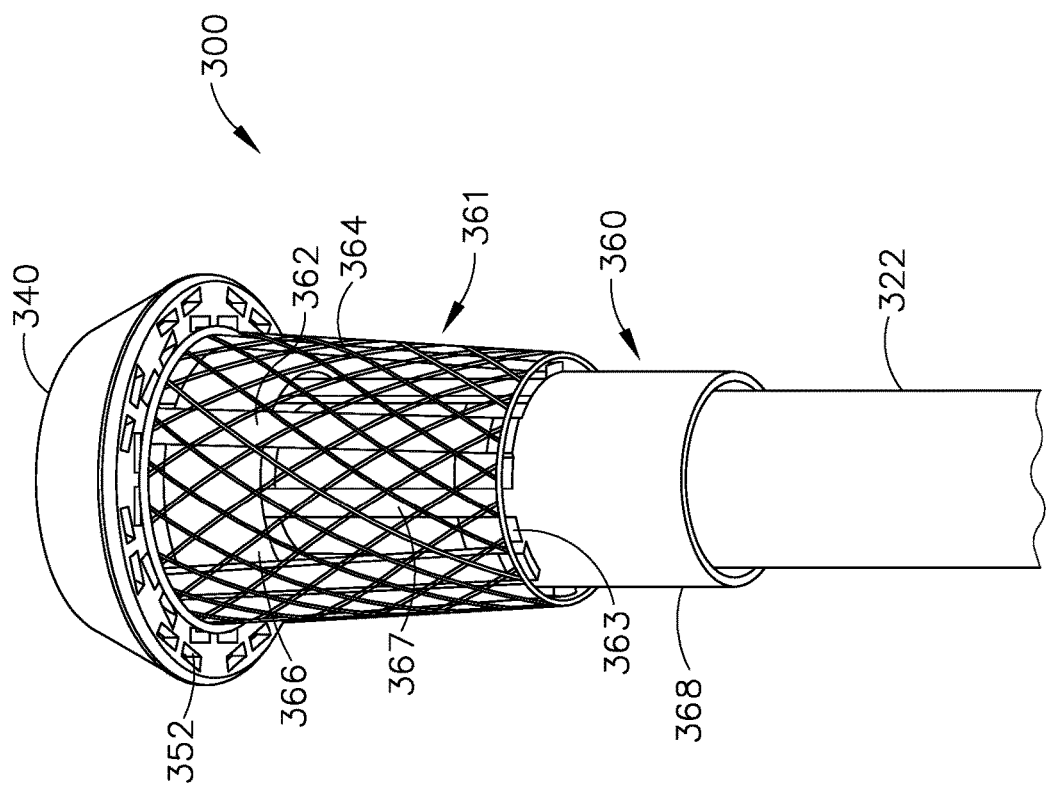
FIG. 15 depicts an enlarged partial perspective view of the anvil introduction system of FIG. 11 showing the dilation feature in a collapsed state with a mesh covering.

Another exemplary trans-oral circular anvil introduction system (300) comprising a dilation feature is shown in FIGS. 11-17B. Anvil introduction system (300) comprises an anvil (340), a flexible tube (322), a sliding feature (360), and a dilation feature (361). Anvil (340) is similar to anvil (40) described above. Anvil (340) comprises staple pockets (352) aligned on proximal surface (350) of anvil (340), as shown in FIG. 15. Anvil (340) also comprises a shaft (344) extending from proximal surface (350) of anvil (340). Shaft (344) is similar to proximal shaft (42) of anvil (40) such that shaft (344) is configured to couple with trocar (38) once anvil (340) is positioned for stapling. Shaft (344) is coupled to flexible tube (322) as anvil (340) is being moved into a position for stapling. Shaft (344) comprises a smaller diameter than flexible tube (322) such that shaft (344) slides into flexible tube (322) to couple flexible tube (322) to anvil (340). Shaft (344) may also have a larger diameter than flexible tube (322) such that shaft (344) may slide around flexible tube (322). Shaft (344) may also be sutured to flexible tube (322) through corresponding apertures (312, 320) in shaft (344) and flexible tube (322). Other suitable methods to couple flexible tube (322) to shaft (344) will be apparent to one with ordinary skill in the art based on the teachings herein. Flexible tube (322) may comprise a conventional NG (naso-gastric) tube or any other suitable structure.

Figure 11:
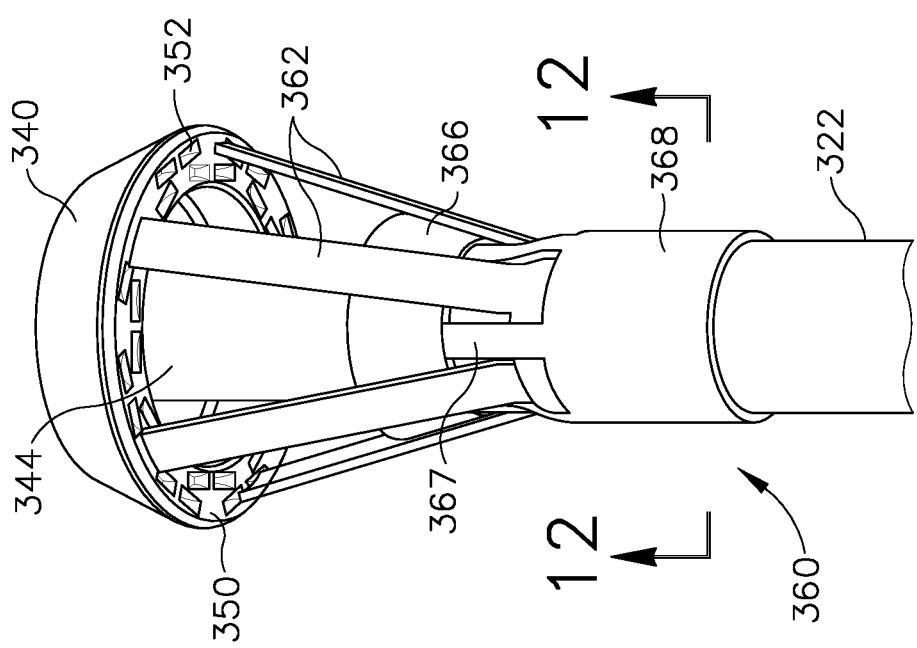
FIG. 11 depicts an enlarged partial perspective view of another exemplary trans-oral circular anvil introduction system showing a dilation feature in an expanded state.

Sliding feature (360) is coupled to flexible tube (322). Sliding feature (360) comprises a sliding collar (368), connecting members (367), and a cam collar (366), as shown in FIG. 11. Sliding collar (368) wraps around flexible tube (322) such that sliding collar (368) slides proximally and/or distally along flexible tube (322). A cam collar (366) is positioned distal to sliding collar (368) and cam collar (366) also wraps around flexible tube (322) such that cam collar (366) slides proximally and/or distally along flexible tube (322). Cam collar (366) defines a tapered configuration. One or more connecting members (367) extend between sliding collar (368) and cam collar (366) to connect sliding collar (368) to cam collar (366).

Figure 13:
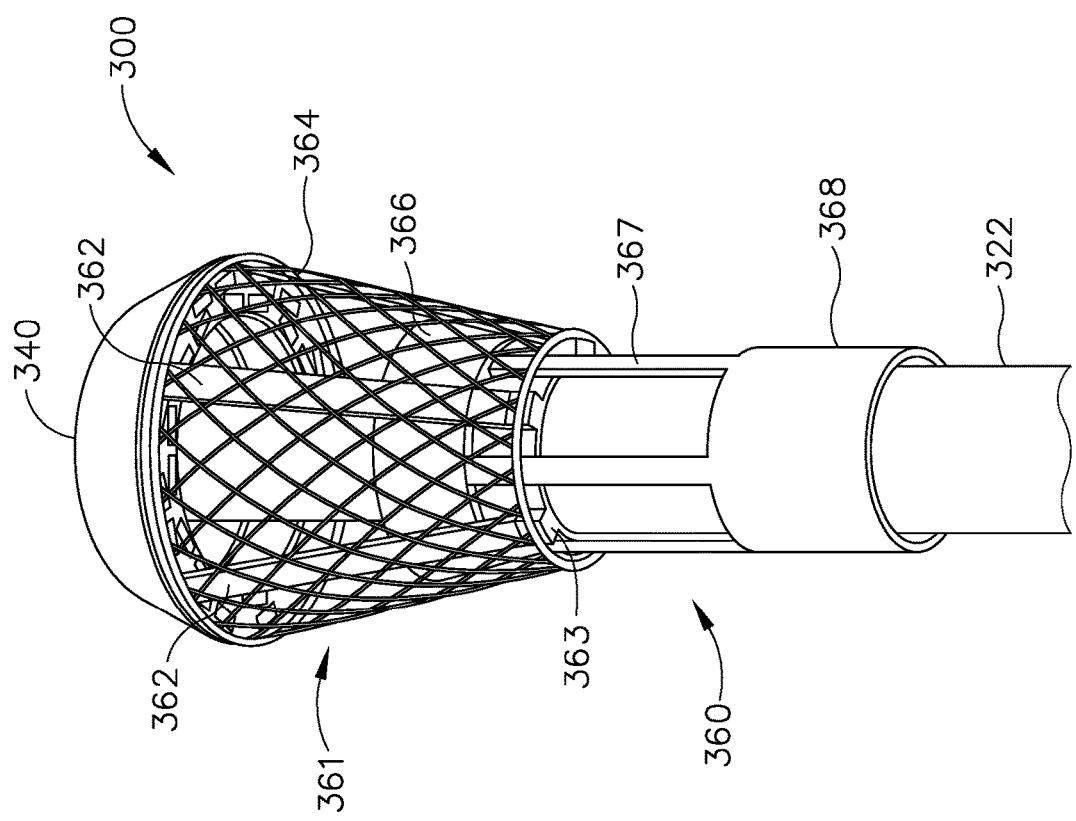
FIG. 13 depicts an enlarged partial perspective view of the anvil introduction system of FIG. 11 showing the dilation feature in the expanded state with a mesh covering.

Dilation feature (361) is also coupled to flexible tube (322), as shown in FIGS. 13-14. Dilation feature (361) comprises expanding members (362) and a washer (363). Washer (363) wraps around flexible tube (322) such that washer (363) is positioned between cam collar (366) and sliding collar (368). Washer (363) is fixed relative to flexible tube (322) such that sliding feature (360) also slides relative to washer (363). A plurality of expanding members (362) extend distally from washer (363) to anvil (340). Expanding members (362) are positioned to extend from underneath sliding collar (368) and over cam collar (366), as shown in FIG. 11. A mesh (364) is applied to dilation feature (361) to cover expanding members (362). Mesh (364) is configured to taper from anvil (340) to washer (363). Mesh (364) expands and contracts with expanding members (362). In the present example, mesh (364) extends up to the bottom of the head of anvil (340). In some other versions, mesh (364) fully encompasses the head of anvil (340). In addition or in the alternative, mesh (364) may fully encompass the shaft of anvil (340).

Figure 16:
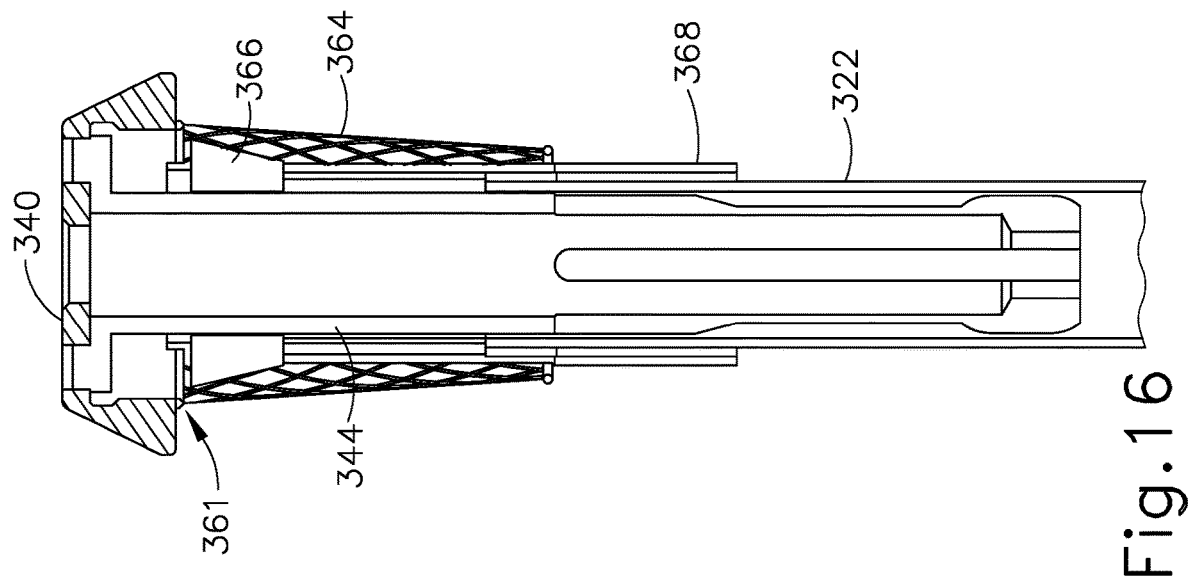
FIG. 16 depicts a cross sectional view of the anvil introduction system of FIG. 15.
Figure 17A:
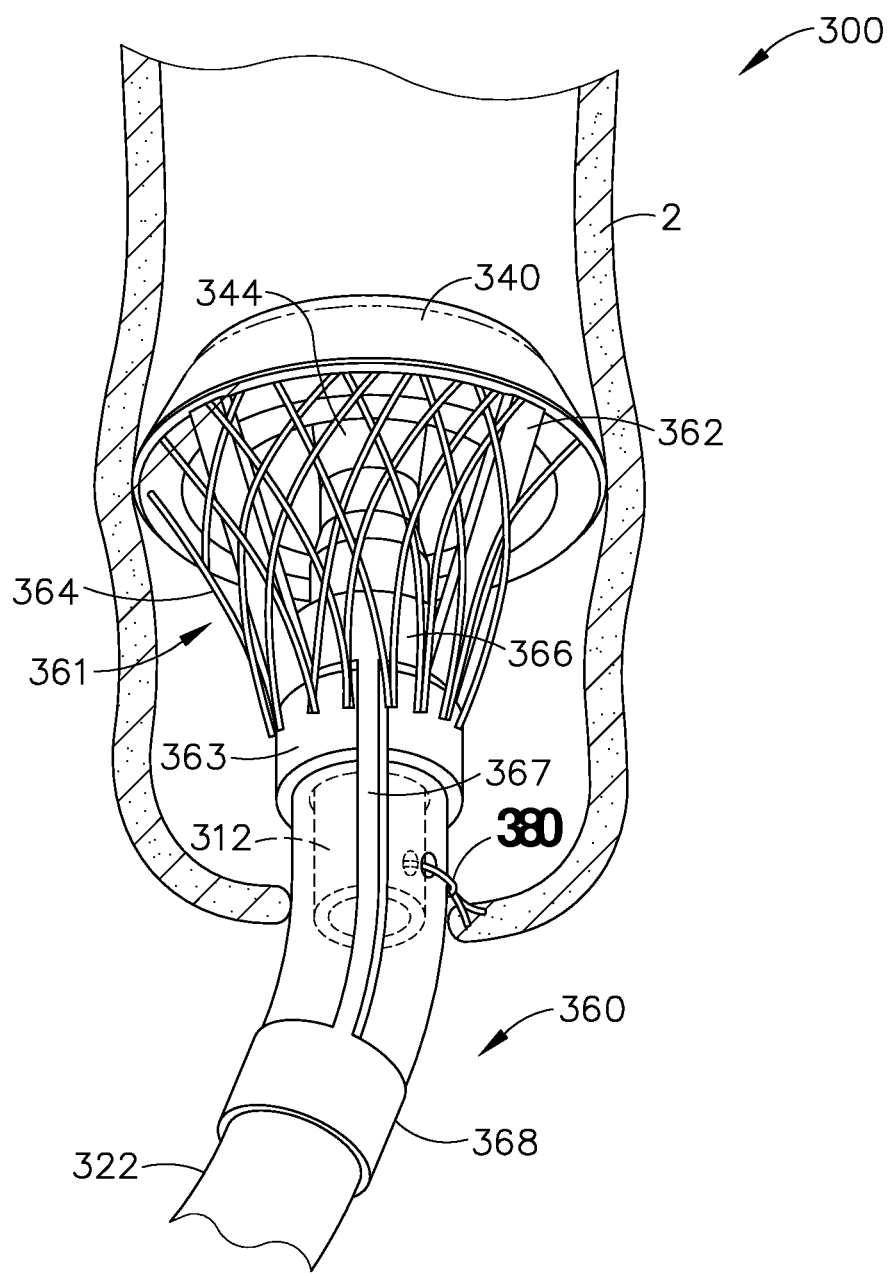
FIG. 17A depicts an enlarged partial perspective view of the anvil introduction system of FIG. 11 passing through a lumen.
Figure 17B:
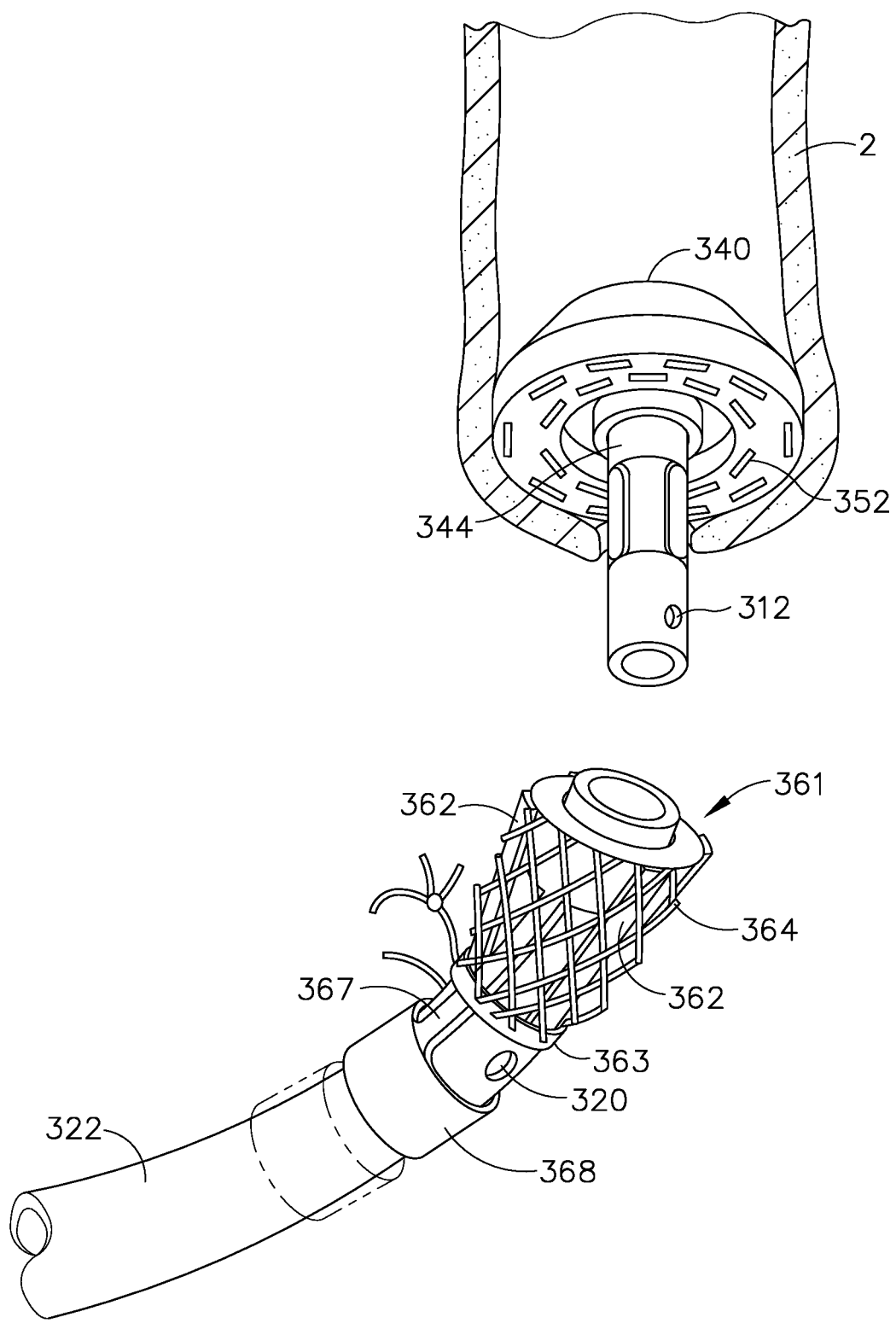
FIG. 17B depicts an enlarged partial perspective view of the anvil introduction system of FIG. 11, showing the anvil introduction system removed from the anvil.

As shown in FIGS. 15-16, flexible tube (322) is coupled to anvil (340) via shaft (344), with dilation feature (361) in a collapsed state. Expanding members (362) and/or mesh (364) may be resiliently biased to assume the collapsed configuration of FIGS. 15-16. In the collapsed state, sliding feature (360) is in a distal position such that cam collar (366) is distal to washer (363). A user grasps sliding collar (368) to translate sliding feature (360) to a proximal position, as shown in FIGS. 13-14. A conventional grasper or any other device may be used to translate sliding collar (368). As sliding collar (368) translates proximally, cam collar (366) also translates proximally to engage washer (363). The tapered configuration of cam collar (366) underneath expanding members (362) acts as a cam, pushing expanding members (362) outwardly to an expanded state. In the expanded state, expanding members (362) contact the edge of proximal surface (350) of anvil (340). Mesh (364) also expands with expanding members (362). In the expanded state, dilation feature (361) covers the edge and staple pockets (352) of anvil (340). With proximal surface (350) of anvil (340) covered by dilation feature (361), anvil (340) is introduced trans-orally by pulling flexible tube (322) of anvil introduction system (300) through the esophagus, as shown in FIG. 17A. When dilation feature (361) is in the expanded position, dilation feature (362) prevents the edge of anvil (340) from dragging along the inner wall of the esophagus. Once anvil (340) is in a desired position within the esophagus, suture (380) connecting flexible tube (322) and anvil shaft (344) is cut. Sliding collar (368) is then advanced distally to allow dilation feature (361) to collapse. As shown in FIG. 17B, flexible tube (322) is then pulled to remove flexible tube (322), sliding feature (360), and dilation feature (361) from anvil (340). Anvil (340) is then coupled to trocar (38) of circular surgical stapling instrument (10) for operation.

B. Exemplary Anvil Grasping Features

An anvil (40) may comprise an anvil grasping features to facilitate pulling anvil (40) upside-down through the esophagus such that the proximal side of anvil (40) faces away from tissue. This may enable a tapered or curved upper surface of anvil (40) to engage tissue as anvil (40) is pulled through the esophagus. A flexible or rigid anvil grasping feature may be used. Various examples of such features will be described in greater detail below, while other examples will be apparent to one with ordinary skill in the art in view of the teachings herein.

1. Exemplary Flexible Grasping Feature

Figure 18:
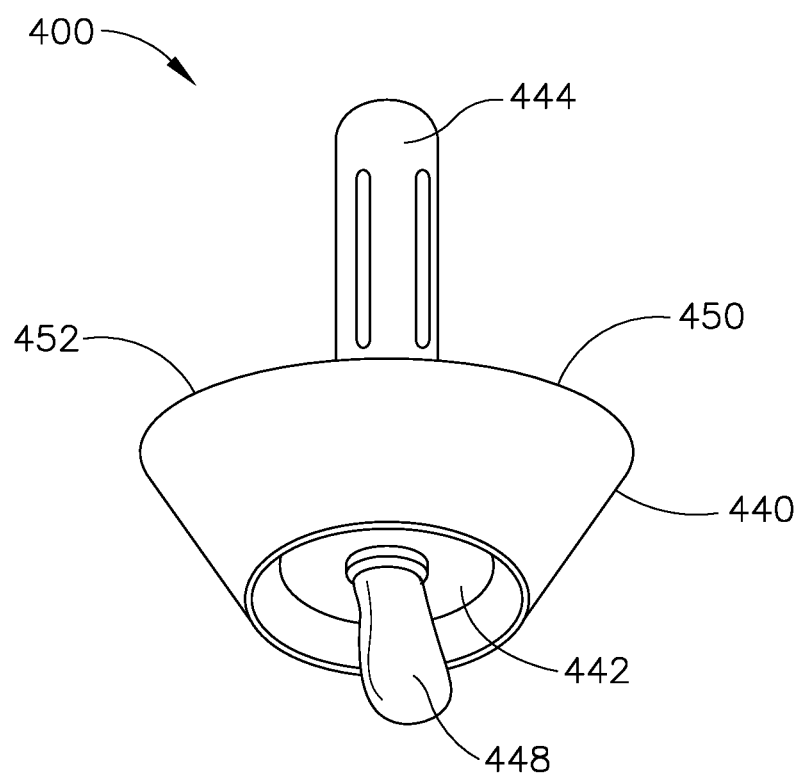
FIG. 18 depicts an enlarged bottom perspective view of an exemplary anvil with a grasping feature.

FIGS. 18-19C show an exemplary anvil assembly (400) comprising an anvil grasping feature (448). Grasping feature (448) is used to grasp anvil (440) at an orientation with top surface (442) leading through a naturally occurring bodily lumen (e.g. the esophagus). Anvil assembly (400) comprises an anvil (440), an anvil grasping feature (448), and an anvil shaft (444), as shown in FIG. 18. Anvil (440) is similar to anvil (40) described above. Anvil (440) comprises staple pockets (452) on lower surface (450) of anvil (440). Shaft (444) extends from lower surface (450) of anvil (440). Shaft (444) is coupleable to trocar (38). Anvil (440) defines a tapered configuration such that top surface (442) comprises a smaller diameter than lower surface (450). Grasping feature (448) extends from top surface (442) of anvil (440). Grasping feature (448) may be flexible. As shown in FIG. 18, grasping feature (448) is configured as a rounded tab. Grasping feature (448) may also be configured as a long, round cylindrical tab, or a flat fin shaped tab. Other suitable grasping configurations will be apparent to one with ordinary skill in the art in view of the teachings herein.

In an exemplary use, as shown in FIGS. 19A-19C, anvil (440) is introduced by leading top surface (442) trans-orally through the esophagus. The tapered configuration defined by anvil (440) provides a smooth transit for anvil (440) through the esophagus. A suture (450) is coupled around shaft (444)

of anvil (440). A conventional surgical grasper (460) is used to grab grasping feature (448) with grasping end effector jaws (462), as shown in FIG. 19A. Grasper (460) is then pulled through the esophagus to trans-orally introduce anvil (440) to the intended anastomosis site. Once anvil (440) is close to a desired positioned within the esophagus, grasper (460) releases grasping feature (448). As shown in FIG. 19B, grasper (460) then grabs suture (450) to pull anvil shaft (444) to thereby flip anvil (440) to align lower surface (450) with the desired tissue (2) to be stapled. After anvil (440) is flipped, grasper (460) continues to pull anvil (440) into position, as shown in FIG. 19C. Suture (350) is then cut and grasper (460) is removed. Anvil (440) is then coupled to trocar (38) of circular surgical stapling instrument (10) for operation.

2. Exemplary Rigid Grasping Feature

Figure 20:
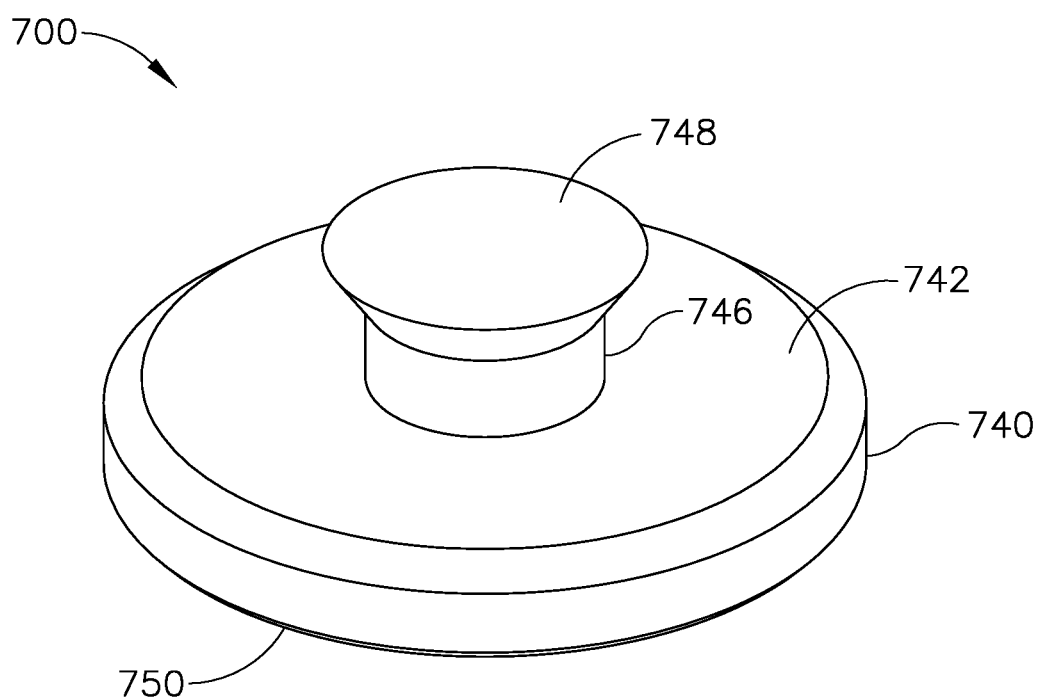
FIG. 20 depicts an enlarged top perspective view of another exemplary anvil with a grasping feature.
Figure 21A:
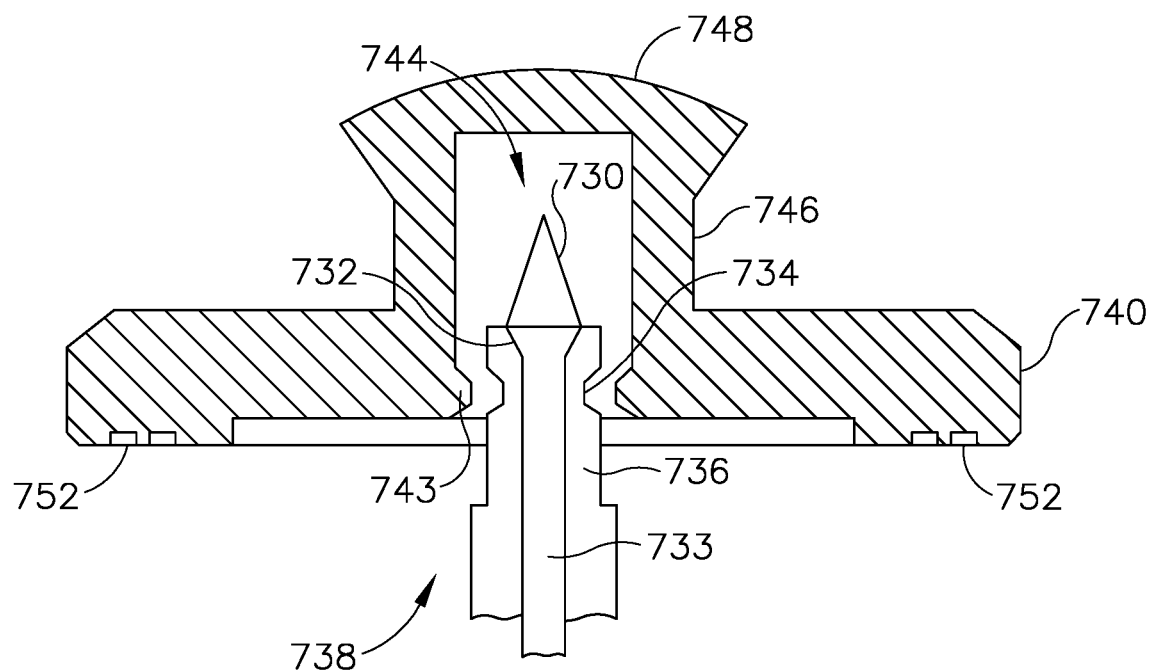
FIG. 21A depicts a cross sectional view of the anvil of FIG. 20, showing an anvil locking feature in a collapsed state.
Figure 21B:
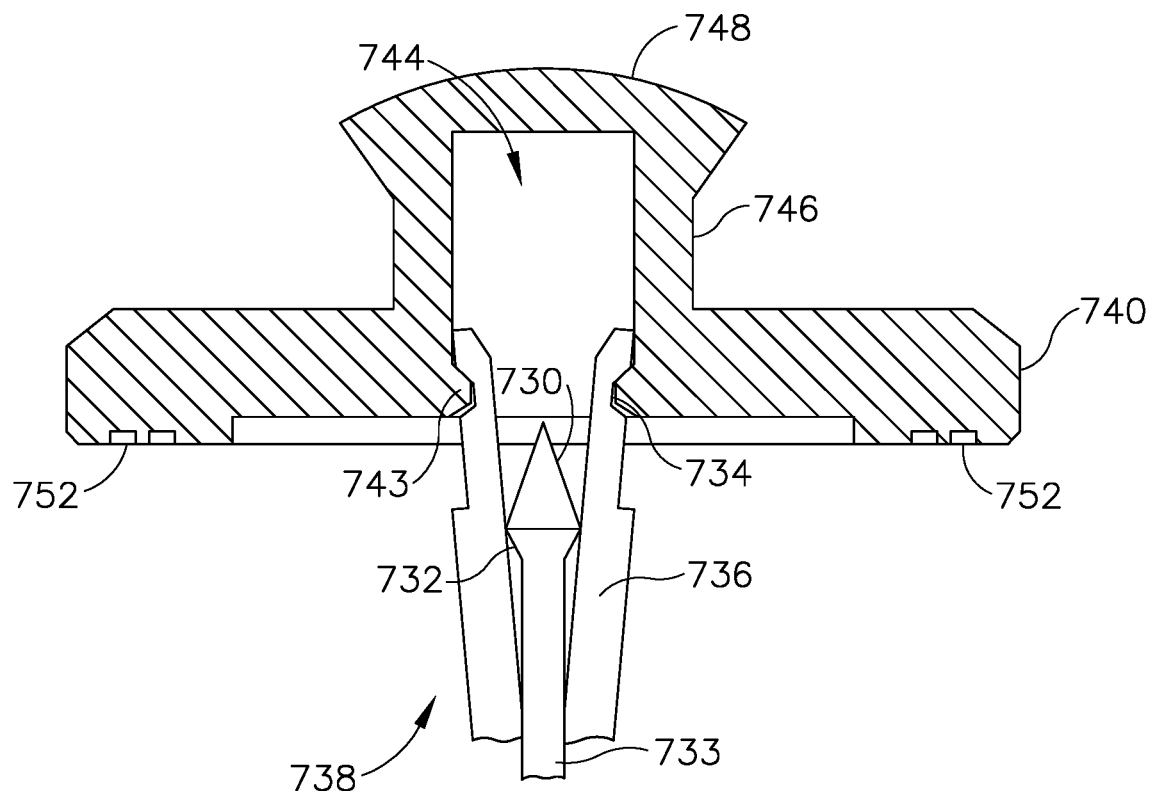
FIG. 21B depicts a cross sectional view of the anvil of FIG. 20, showing the anvil locking feature in an expanded state.

FIGS. 20-21B show another exemplary anvil assembly (700) comprising an anvil grasping feature (748). Anvil assembly (700) comprises an anvil (740) and an anvil grasping feature (748), as shown in FIG. 20. Anvil (740) is similar to anvil (40) described above. Anvil (740) comprises staple pockets (752) on lower surface (750) of anvil (740). A shaft (746) extends from top surface (742) of anvil (740) to connect anvil grasping feature (748) to anvil (740). Anvil grasping feature (748) comprises a convex shaped top. An opening (744) is formed on lower surface (750) of anvil (740) to receive trocar (738), as shown in FIG. 21A. Opening (744) comprises an inwardly extending annular protrusion (743).

Trocar (738) is similar to trocar (38). Trocar (738) comprises a pointed distal end (730), a cam portion (732), a shaft (733), and expanding members (736), as shown in FIG. 21A. The distal portion of shaft (733) is angled to form cam portion (732). Pointed distal end (730) is positioned distal to cam portion (732). Shaft (733) extends through expanding members (736). Expanding members (736) comprise inwardly extending recesses (734) that correspond to protrusion (743).

In an exemplary use, anvil (740) is introduced by leading top surface (742) through a naturally occurring bodily lumen (e.g. the esophagus). A grasper is used to grab grasping feature (748) with jaws to pull anvil (740) trans-orally through the esophagus. Anvil (740) is flipped to align lower surface (750) with tissue (2) to be stapled. Once anvil (740) is positioned within the esophagus, anvil (740) is coupled to trocar (738) for operation. In particular, trocar (738) is inserted into opening (744) of anvil (740) until recesses (734) align with protrusion (743), as shown in FIG. 21A. Shaft (733) is pulled proximally to slide shaft (733) through expanding members (736). As shaft (733) translates proximally, cam portion (732) pushes expanding members (736) outwardly, as shown in FIG. 21B. This causes recesses (734) to engage protrusion (743). The longitudinal position of shaft (733) relative to expanding members (736) is secured in order to cause recesses (734) of trocar (738) to lock anvil (740) to trocar (738) during operation of circular surgical stapling instrument (10). After operation of instrument (10), shaft (733) may be translated distally to allow expanding members (736) to bend inwardly. This removes recesses (734) from protrusion (743) to unlock anvil (740) from trocar (738). Instrument (10) and anvil (740) may then be removed separately from the anastomosis site. Alternatively, instrument (10) may be removed from the anastomosis site with anvil (740) still coupled to trocar (738).

C. Exemplary Anvil Securing Feature

An anvil securing feature (848) may be applied to the various anvils, including those described above, to hold anvil (840) in place relative to tissue while coupling anvil (840) to a trocar (38). An exemplary anvil assembly (800) comprising an anvil securing feature (848) is shown in FIGS. 22A-22B. Anvil assembly (800) comprises an anvil (840) and an anvil securing feature (848). Anvil (840) is similar to anvil (40) described above. Anvil (840) comprises staple pockets (852) on lower surface (850) of anvil (840). A shaft (844) extends from lower surface (850) of anvil (840). Anvil securing feature (848) is fixedly coupled to shaft (844). Anvil securing feature (848) comprises a collar (822) and a flange (820) extending from collar (822), as shown in FIG. 22A. Collar (822) is configured to wrap around shaft (844) to couple anvil securing feature (848) to anvil (840). An opening (824) is formed in flange (820) such that a suture may pass through opening (824). Alternatively, flange (820) may be formed of a compliant material to enable needle (832) to pierce flange (820) at any desired location on flange (820).

Once anvil (840) is positioned within through the esophagus using any of the features described above, anvil securing feature (848) allows for retention of anvil (840) relative to tissue after a grasper is removed from anvil (840). As shown in FIGS. 22A-22B, tissue (2) is sutured in a purse-string configuration. Suture (830) then passes through opening (824) of anvil securing feature (848) by needle (832). A loop is formed through opening (824) around flange (820) with suture (830). As suture (830) is drawn around tissue (2) and flange (820), anvil (840) is held in position by suture (830). With anvil (840) secured to tissue (2), anvil (840) is held in place when anvil (840) is coupled to a trocar (38). Other suitable suturing methods to retain anvil (840) will be apparent to one with ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue, the apparatus comprising:
   (a) an anvil, wherein the anvil comprises:
      (i) a distal surface,
      (ii) a proximal surface,
      (iii) a plurality of staple pockets, wherein the plurality of staple pockets are formed on the proximal surface of the anvil, and
      (iv) a shaft comprising a distal end and an open proximal end, wherein the shaft extends from the proximal surface;
      wherein the anvil is configured to be inserted through a bodily lumen; and
   (b) an anvil introduction system coupled with the anvil, wherein the anvil introduction system comprises:
      (i) a flexible tube configured selectively couple with the shaft at the open proximal end, and
      (ii) a dilation feature comprising an inflatable bladder, wherein the inflatable bladder comprises a portion fixed to the shaft of the anvil such that the inflatable bladder surrounds a portion of the shaft, wherein the flexible tube is configured to transition the dilation feature between a collapsed position and an expanded position, wherein the dilation feature is configured to cover the staple pockets of the anvil in the expanded position, wherein the dilation feature is configured to be in the expanded position when the anvil is inserted through the bodily lumen.

2. The apparatus of claim 1, wherein the shaft is hollow and defines an aperture in fluid communication with an interior of the inflatable bladder.

3. The apparatus of claim 2, wherein the flexible tube is configured to be in fluid communication with an interior of the shaft when the flexible tube is coupled with the open proximal end of the shaft.

4. The apparatus of claim 3, wherein the flexible tube is configured to inject fluid into the inflatable bladder via the interior of the shaft and the aperture to transition the dilation feature between a collapsed position and the expanded position.

5. The apparatus of claim 1, wherein the flexible tube is configured to selectively couple with the shaft via a snap fit feature.

6. An apparatus for stapling tissue, the apparatus comprising:
   (a) an anvil, wherein the anvil comprises:
      (i) a distal end,
      (ii) a proximal end,
      (iii) a distal surface extending from the distal end,
      (iv) a proximal surface,
      (v) a plurality of staple pockets, wherein the plurality of staple pockets are formed on the proximal surface of the anvil, and
      (vi) a shaft extending from the proximal surface and terminating at the proximal end;
      wherein the anvil is configured to be inserted through a bodily lumen; and
   (b) an anvil introduction system coupled with the anvil, wherein the anvil introduction system comprises a dilation feature, wherein the dilation feature comprises an inflatable bladder, wherein a portion of the inflatable bladder is fixed with a portion of the shaft such that the portion of the inflatable bladder surrounds the portion of the shaft, wherein the dilation feature is configured to transition between a collapsed position and an expanded position, wherein the dilation feature is configured to cover the staple pockets of the anvil in the expanded position, wherein the dilation feature terminates proximal to the distal end of the anvil, wherein the dilation feature is configured to be in the expanded position when the anvil is inserted through the bodily lumen.

7. An apparatus for stapling tissue, the apparatus comprising:
   (a) an anvil, wherein the anvil comprises:
      (i) a distal surface,
      (ii) a proximal surface, and
      (iii) a plurality of staple pockets, wherein the plurality of staple pockets are formed on the proximal surface of the anvil, and
      wherein the anvil is configured to be inserted through a bodily lumen; and (b) an anvil introduction system comprising an inflatable bladder coupled with the anvil such that the inflatable bladder is in fluid communication with the anvil via an aperture defined in the anvil, wherein the inflatable bladder is configured to transition between a collapsed position and an expanded position based on fluid communication from the aperture, wherein the inflatable bladder is configured to cover the staple pockets of the anvil in the expanded position without covering the entire anvil, wherein the inflatable bladder terminates proximal to the distal surface, wherein the inflatable bladder is configured to be in the expanded position when the anvil is inserted through the bodily lumen.

8. The apparatus of claim 7, wherein the anvil further comprises a hollow shaft defining a lumen.

9. The apparatus of claim 7, wherein the inflatable bladder is in fluid communication with the hollow shaft via the lumen and the aperture.

\* \* \* \* \*